(12) United States Patent
Lee et al.

(10) Patent No.: US 11,116,551 B2
(45) Date of Patent: Sep. 14, 2021

(54) LAMINA IMPLANTS AND METHODS FOR SPINAL DECOMPRESSION

(71) Applicant: DePuy Synthes Products, Inc., Raynham, MA (US)

(72) Inventors: Kevin Lee, Canton, MA (US); Albert Montello, Duxbury, MA (US); Todd James Albert, New York, NY (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 16/452,503

(22) Filed: Jun. 25, 2019

(65) Prior Publication Data

US 2019/0314063 A1    Oct. 17, 2019

Related U.S. Application Data

(60) Continuation of application No. 15/634,833, filed on Jun. 27, 2017, now Pat. No. 10,342,584, which is a
(Continued)

(51) Int. Cl.
*A61B 17/70* (2006.01)
*A61B 17/16* (2006.01)
(Continued)

(52) U.S. Cl.
CPC ...... *A61B 17/7071* (2013.01); *A61B 17/1671* (2013.01); *A61B 17/1757* (2013.01);
(Continued)

(58) Field of Classification Search
CPC .................................................. A61B 17/7071
See application file for complete search history.

(56) References Cited

U.S. PATENT DOCUMENTS

| 5,437,669 A | 8/1995 | Yuan et al. |
| 5,470,333 A | 11/1995 | Ray |

(Continued)

FOREIGN PATENT DOCUMENTS

| CN | 2880012 Y | 3/2007 |
| CN | 101785694 B | 11/2011 |

(Continued)

OTHER PUBLICATIONS

**Extended European Search Report for Application No. 16162694.0, dated Aug. 4, 2016 (9 pages).
(Continued)

*Primary Examiner* — Julianna N Harvey
(74) *Attorney, Agent, or Firm* — Barnes & Thornburg LLP

(57) ABSTRACT

Lamina plates can include various features that allow a surgeon to couple the plate to a vertebra, such as a plurality of receiving holes for receiving a spinal fixation element. The plate can be shaped and the receiving holes positioned such that spinal fixation elements can be installed with reduced exposure of the spine and along a trajectory that enhances purchase with bone. The lamina plate can include one or more features for coupling at least one receiver head to the plate for receiving a spinal stabilization element. Since the receiver head can be coupled to the plate after the plate is implanted, it does not restrict the range of angles or trajectories at which the spinal fixation elements can be installed.

23 Claims, 19 Drawing Sheets

Related U.S. Application Data division of application No. 14/684,498, filed on Apr. 13, 2015, now Pat. No. 9,717,541.

(51) Int. Cl.
*A61B 17/17* (2006.01)
*A61B 17/86* (2006.01)

(52) U.S. Cl.
CPC ...... *A61B 17/7011* (2013.01); *A61B 17/7013* (2013.01); *A61B 17/7059* (2013.01); *A61B 17/8605* (2013.01); *A61B 2017/8655* (2013.01)

(56) References Cited

U.S. PATENT DOCUMENTS

| | | | |
|---|---|---|---|
| 5,980,572 A | 11/1999 | Kim et al. | |
| 6,080,157 A | 6/2000 | Cathro et al. | |
| 6,419,703 B1 | 7/2002 | Fallin et al. | |
| 6,458,131 B1 | 10/2002 | Ray | |
| 6,481,440 B2 | 11/2002 | Gielen et al. | |
| 6,635,087 B2 | 10/2003 | Angelucci et al. | |
| 6,669,729 B2 | 12/2003 | Chin | |
| 6,902,580 B2 | 6/2005 | Fallin et al. | |
| 7,090,698 B2 | 8/2006 | Goble et al. | |
| 7,220,262 B1 | 5/2007 | Hynes | |
| 7,282,064 B2 | 10/2007 | Chin | |
| 7,377,942 B2 | 5/2008 | Berry | |
| 7,604,652 B2 | 10/2009 | Amin et al. | |
| 7,717,939 B2 | 5/2010 | Ludwig et al. | |
| 7,837,711 B2 | 11/2010 | Bruneau et al. | |
| 7,850,732 B2 | 12/2010 | Heinz | |
| 7,857,833 B2 | 12/2010 | Abdou | |
| 7,862,590 B2 | 1/2011 | Lim et al. | |
| 8,002,801 B2 | 8/2011 | Carl et al. | |
| 8,066,741 B2 | 11/2011 | Fallin et al. | |
| 8,105,366 B2 | 1/2012 | Null et al. | |
| 8,167,917 B2 | 5/2012 | Chin et al. | |
| 8,226,688 B2 | 7/2012 | Alain | |
| 8,246,660 B2 | 8/2012 | Boris et al. | |
| 8,252,026 B2 | 8/2012 | Joshi | |
| 8,303,631 B2 | 11/2012 | Duggal et al. | |
| 8,348,976 B2 | 1/2013 | Kohm et al. | |
| 8,348,977 B2 | 1/2013 | Bruneau et al. | |
| 8,377,103 B2 | 2/2013 | Reiley | |
| 8,414,624 B2 | 4/2013 | Currier et al. | |
| 8,430,911 B2 | 4/2013 | Chin et al. | |
| 8,470,000 B2 | 6/2013 | Trautwein et al. | |
| 8,518,081 B2 | 8/2013 | Patel et al. | |
| 8,679,160 B2 | 3/2014 | Jensen et al. | |
| 9,138,325 B2 | 9/2015 | Mouw | |
| 9,198,696 B1 | 12/2015 | Bannigan et al. | |
| 9,247,964 B1 | 2/2016 | Shoshtaev | |
| 9,301,787 B2 | 4/2016 | Malek | |
| 9,498,346 B2 | 11/2016 | Beger et al. | |
| 9,717,541 B2 | 8/2017 | Lee et al. | |
| 10,342,584 B2 | 7/2019 | Lee et al. | |
| 2003/0040797 A1 | 2/2003 | Fallin et al. | |
| 2003/0050700 A1 | 3/2003 | Kihara | |
| 2004/0030388 A1 | 2/2004 | Null et al. | |
| 2004/0158245 A1 | 8/2004 | Chin | |
| 2004/0210222 A1 | 10/2004 | Angelucci et al. | |
| 2005/0033434 A1 | 2/2005 | Berry | |
| 2005/0119657 A1 | 6/2005 | Goldsmith | |
| 2006/0036246 A1 | 2/2006 | Carl et al. | |
| 2006/0036324 A1 | 2/2006 | Sachs et al. | |
| 2006/0058790 A1 | 3/2006 | Carl et al. | |
| 2006/0241610 A1 | 10/2006 | Lim et al. | |
| 2007/0191834 A1 | 8/2007 | Bruneau et al. | |
| 2007/0198091 A1 | 8/2007 | Boyer et al. | |
| 2007/0233068 A1 | 10/2007 | Bruneau et al. | |
| 2008/0021454 A1 | 1/2008 | Chao et al. | |
| 2008/0027549 A1 | 1/2008 | Kirschman | |
| 2008/0215096 A1 | 9/2008 | Nash et al. | |
| 2008/0281360 A1 | 11/2008 | Vittur et al. | |
| 2008/0281361 A1 | 11/2008 | Vittur et al. | |
| 2008/0306537 A1 | 12/2008 | Culbert | |
| 2009/0018585 A1 | 1/2009 | Reiley | |
| 2009/0171394 A1 | 7/2009 | Abdou | |
| 2009/0318968 A1* | 12/2009 | Duggal ............ A61B 17/7043 606/250 |
| 2010/0057127 A1 | 3/2010 | McGuire et al. | |
| 2010/0063590 A1 | 3/2010 | Cannestra | |
| 2010/0069960 A1 | 3/2010 | Chaput | |
| 2010/0070034 A1 | 3/2010 | Durward et al. | |
| 2010/0174315 A1 | 7/2010 | Scodary et al. | |
| 2010/0185240 A1 | 7/2010 | Mangione et al. | |
| 2010/0249842 A1 | 9/2010 | Mir | |
| 2010/0268277 A1 | 10/2010 | Bruneau et al. | |
| 2010/0324599 A1 | 12/2010 | Montello et al. | |
| 2011/0093012 A1 | 4/2011 | Gittings | |
| 2011/0106168 A1 | 5/2011 | Bucci et al. | |
| 2011/0125269 A1* | 5/2011 | Moskowitz ........ A61B 17/7071 623/17.11 |
| 2011/0144692 A1 | 6/2011 | Saladin et al. | |
| 2011/0160772 A1 | 6/2011 | Arcenio et al. | |
| 2011/0172709 A1 | 7/2011 | Lyons et al. | |
| 2011/0178552 A1 | 7/2011 | Biscup et al. | |
| 2011/0270397 A1 | 11/2011 | Mac-Thiong | |
| 2011/0307012 A1 | 12/2011 | Mir et al. | |
| 2011/0313465 A1 | 12/2011 | Warren et al. | |
| 2012/0016417 A1 | 1/2012 | Druma | |
| 2012/0016419 A1 | 1/2012 | Aflatoon | |
| 2012/0035728 A1 | 2/2012 | Fallin et al. | |
| 2012/0059476 A1 | 3/2012 | Fallin et al. | |
| 2012/0071923 A1 | 3/2012 | Perez-Cruet et al. | |
| 2012/0078303 A1 | 3/2012 | Malek | |
| 2012/0078304 A1 | 3/2012 | Jensen et al. | |
| 2012/0095509 A1 | 4/2012 | Jensen et al. | |
| 2012/0143253 A1 | 6/2012 | Reiley | |
| 2012/0143337 A1 | 6/2012 | Jensen et al. | |
| 2012/0158060 A1 | 6/2012 | Abrahams et al. | |
| 2012/0165942 A1 | 6/2012 | Khanna | |
| 2012/0209328 A1 | 8/2012 | Alamin et al. | |
| 2012/0215261 A1 | 8/2012 | Massoudi | |
| 2012/0259363 A1 | 10/2012 | Lange et al. | |
| 2012/0259364 A1 | 10/2012 | Lange | |
| 2012/0259366 A1 | 10/2012 | Lange | |
| 2012/0259367 A1 | 10/2012 | Lange | |
| 2012/0265252 A1 | 10/2012 | Stinson et al. | |
| 2012/0271359 A1 | 10/2012 | Stevenson et al. | |
| 2012/0296377 A1 | 11/2012 | Ferree et al. | |
| 2012/0316647 A1 | 12/2012 | Farin | |
| 2013/0030472 A1 | 1/2013 | Williams | |
| 2013/0053886 A1 | 2/2013 | Hawkins et al. | |
| 2013/0053892 A1* | 2/2013 | Hawkins ............ A61B 17/7037 606/264 |
| 2013/0060283 A1 | 3/2013 | Suh et al. | |
| 2013/0197641 A1 | 8/2013 | Shepard et al. | |
| 2013/0211524 A1 | 8/2013 | Hugues | |
| 2014/0018920 A1* | 1/2014 | Mouw ................ A61B 17/707 623/17.11 |
| 2014/0142699 A1* | 5/2014 | Beger ................ A61B 17/1757 623/17.11 |
| 2014/0277140 A1* | 9/2014 | Jarolem ................ A61B 17/86 606/247 |
| 2016/0296259 A1 | 10/2016 | Lee et al. | |
| 2017/0290613 A1 | 10/2017 | Lee et al. | |

FOREIGN PATENT DOCUMENTS

| | | |
|---|---|---|
| CN | 102247207 A | 11/2011 |
| CN | 202051805 U | 11/2011 |
| CN | 102366335 A | 3/2012 |
| CN | 102551923 A | 7/2012 |
| CN | 202288441 U | 7/2012 |
| CN | 202665673 U | 1/2013 |
| FR | 2761876 A1 | 10/1998 |
| JP | 2011245061 A | 12/2011 |
| KR | 10-0942170 B1 | 2/2010 |
| WO | 2004/098465 A1 | 11/2004 |
| WO | 2007/149634 A2 | 12/2007 |

(56) References Cited

FOREIGN PATENT DOCUMENTS

WO    2008/016970 A2    2/2008
WO    2011/040983 A1    4/2011

OTHER PUBLICATIONS

\*\*Oglesby, M., et al., Epidemiological trends in cervical spine surgery for degenerative diseases between 2002 and 2009. Spine (Phila Pa 1976). Jun. 15, 2013;38(14):1226-32. doi: 10.1097/BRS.0b013e31828be75d.

\*\*Sangala, J.R., et al., Technique to minimize paraspinal muscle atrophy after posterior cervical fusion. Clin Neurol Neurosurg. Jan. 2011;113(1):48-51. doi: 10.1016/j.clineuro.2010.09.001. Epub Oct. 16, 2010.

Japanese Office Action for Application No. 2017553335, dated Dec. 17, 2019 (7 pages).

International Search Report and Written Opinion for International Application No. PCT/US2016/025604, dated Jul. 5, 2016 (14 pages).

U.S. Appl. No. 14/684,498, filed Apr. 13, 2015, Lamina Implants and Methods for Spinal Decompression.

U.S. Appl. No. 15/634,833, filed Jun. 27, 2017, Lamina Implants and Methods for Spinal Decompression.

\* cited by examiner

LAMINA IMPLANTS AND METHODS FOR SPINAL DECOMPRESSION

CROSS-REFERENCE TO RELATED APPLICATIONS

The present application is a continuation of U.S. application Ser. No. 15/634,833, filed Jun. 27, 2017, entitled "LAMINA IMPLANTS AND METHODS FOR SPINAL DECOMPRESSION." U.S. application Ser. No. 15/634,833 is a divisional of U.S. application Ser. No. 14/684,498, filed Apr. 13, 2015, entitled "LAMINA IMPLANTS AND METHODS FOR SPINAL DECOMPRESSION." The entire contents of each of these applications is incorporated by reference herein.

FIELD

The present disclosure relates to spinal decompression and fixation systems, in particular, lamina implants and methods for implanting the same in a vertebra.

BACKGROUND

A laminectomy is a surgical procedure performed on the spine to relieve pressure on the spinal cord or one or more nerves. Pressure on the spinal cord or on a nerve can cause various symptoms, such as neck and back pain and/or radicular pain in the arms and legs. Upon removing the lamina, the compressed nerves can be exposed and pressure on the nerves can be further relieved by removing the source of compression, such as a portion of the disc, a disc fragment, a tumor, or a rough protrusion of bone.

Spinal fixation procedures can be performed in conjunction with a laminectomy to align and/or fix desired relationships between adjacent vertebral bodies. Such spinal fixation procedures typically include positioning a plurality of spinal fixation assemblies within target vertebrae. These assemblies usually include a threaded shank portion configured to be disposed (e.g., threaded) within a vertebra and a proximal receiver head configured to receive and secure some type of spinal stabilization element (e.g., a rigid or flexible rod, a cable, a biological construct, a tether, a tape, etc.). Once these assemblies are disposed within the desired vertebrae, a spinal stabilization rod can be positioned and secured within the receiver heads thereby allowing the rod to extend along a length of the patient's spinal column. Once secured as such, the installed spinal stabilization rod can hold the vertebrae in the desired spatial relationship, either until desired healing or spinal fusion has taken place, or for some longer period of time.

Due to the intricacies of working in proximity to the spinal column, such laminectomies and spinal fixation procedures can cause serious patient injury and/or significant patient trauma. For example, such procedures typically require spinal fixation assemblies to be delivered directly (i.e., substantially perpendicular to the midline of the patient's spinal column) into a lateral mass or pedicle of a target vertebra. In light of this trajectory, significant amounts of muscle and tissue must be stripped from the treatment site due to the relatively large distance between the lateral mass/pedicle entry point and the midline of the spinal column. Also, any slight miscalculation in the delivery trajectory can result in penetration of a distal portion of the assembly (e.g., a pointed tip) into the spinal canal or the foramina of the exiting nerve root thereby causing significant patient injury. As a further disadvantage, the limited bone mass and/or bone density typically found in the lateral mass portion of a vertebra significantly limits the amount of area available for contacting the fixation assembly thereby hindering the ability to effectively position the fixation assembly within the vertebra.

Thus, there remains a need for methods and systems for spinal decompression and/or for securely positioning fixation assemblies within target vertebrae while also minimizing the risk of injury and associated patient trauma.

SUMMARY

Devices, systems, and methods for reducing trauma from spinal stabilization and/or decompression procedures are described herein. Lamina prosthesis plates are provided herein and are configured to be positioned on a vertebra following a laminectomy procedure. In general, a lamina plate can include various features that allow a surgeon to couple the plate to a vertebra, such as a plurality of receiving holes for receiving a spinal fixation element (e.g., a bone screw). The plate can be shaped and the receiving holes positioned such that the spinal fixation elements can be installed with reduced exposure of the spine and along a trajectory that mirrors the anatomy of the bone and enhances purchase with the bone, such as a trajectory that allows for longer fixation elements. In certain aspects, the lamina plate can be curved in an anterior direction to provide space for and prevent injury to the spinal cord. The lamina plate can include one or more features for coupling at least one receiver head to the plate for receiving a spinal stabilization element. One or more receiver heads can be selectively positioned on the lamina plate to allow for stabilization (e.g., midline, unilateral, bilateral, etc.) of a patient's spine. Since the receiver heads can be coupled to the plate after the plate is implanted, they do not restrict the range of angles or trajectories at which the spinal fixation elements can be installed. In cases where spinal stabilization is not desired, the features on the lamina plate for selectively coupling to a receiver head need not be used and the lamina plate can be installed as a stand-alone device for replacing laminae and protecting the spinal cord.

In some embodiments, a spinal implant includes a body having an anterior surface, a posterior surface, a superior surface, and an inferior surface, the body being positionable with respect to a vertebra on which a laminectomy has been performed in an installed position in which a first lateral end of the body receives at least a portion of a first cut lamina end of the vertebra and a second, opposite lateral end of the body receives at least a portion of a second, opposite cut lamina end of the vertebra such that the body spans across the first and second cut lamina ends of the vertebra. The implant can includes a first bone anchor receiving hole formed in the first lateral end of the body and angled such that a bone screw inserted therethrough extends into a first lateral mass of a vertebra when the body is disposed in the installed position with respect to the vertebra. The implant can also include a second bone anchor receiving hole formed in the second lateral end of the body and angled such that a bone screw inserted therethrough extends into a second, opposite lateral mass of a vertebra when the body is disposed in the installed position with respect to the vertebra.

The implant can vary in any number of ways. For example, the implant can include at least one mating feature formed in the body to which a receiver head can be selectively coupled. The at least one mating feature can include a central mating feature disposed along a central superior-inferior axis of the body such that when the body is disposed in the installed position with respect to a vertebra, the central mating feature is positioned above a midline of the vertebra. The at least one mating feature can include first and second lateral mating features positioned laterally offset from a central superior-inferior axis of the body. The at least one mating feature can include threaded holes formed in the body. The superior surface of the body can define a curved relief configured to receive a spinous process of a superior vertebra when the body is disposed in the installed position with respect to an adjacent inferior vertebra. The body can be curved about a central superior-inferior axis of the body such that the anterior surface of the body defines a curved relief for protecting a spinal cord when the body is disposed in the installed position with respect to a vertebra. The implant can include a receiver head having a mating feature configured to selectively couple the receiver head to the at least one mating feature formed in the body. The receiver head can be configured to be coupled to the body via at least one of a polyaxial coupling, a uniplanar coupling, and a monoaxial coupling. The first bone anchor receiving hole can extend at an angle in the range of about 120 degrees to about 140 degrees with respect to a plane in which a posterior-most extent of the body lies.

In some embodiments, a method for decompressing a vertebra includes removing first and second laminae from a vertebra of a patient, thereby forming a first cut end and a second cut end, inserting a lamina plate into the patient such that a first terminal end of the plate contacts the first cut end of the vertebra and a second terminal end of the plate contacts the second cut end of the vertebra, inserting a first screw through a first bone screw hole in the lamina plate and into a first lateral mass of the vertebra, inserting a second screw through a second bone screw hole in the lamina plate and into a second lateral mass of the vertebra to couple the lamina plate to the vertebra, and after inserting the lamina plate into the patient, attaching a receiver head to the lamina plate.

The receiver head can be attached to the lamina plate after the first and second bone screws are inserted through the lamina plate. The receiver head can be attached to one of the first and second bone screws after the first and second bone screws are inserted through the lamina plate. The method can include performing a full laminectomy on a plurality of consecutive vertebral levels of a spine and coupling a lamina plate to each of said consecutive vertebral levels. The method can include attaching a receiver head into each lamina plate. The method can include inserting a spinal stabilization element into the receiver heads. The stabilization element can be positioned above a midline of the spine. The stabilization element can be positioned laterally offset from a midline of the spine. The distance between the first and second cut ends can be in the range of about 15 to about 30 mm. In some embodiments, only about 15 to about 40 mm of the vertebra is exposed lateral to a midline of the vertebra in performing the method.

In some embodiments, a method for treating a vertebra includes inserting a first screw into a first lamina of a vertebra; inserting a second screw into a second lamina of the vertebra; after inserting the first and second screws, removing at least a portion of the first and second laminae, thereby forming a first cut end and a second cut end; partially withdrawing the first and second screws from the vertebra such that the first and second screws protrude from the first and second cut ends, respectively; and attaching a lamina plate to the first and second screws such that a first terminal end of the plate contacts the first cut end of the vertebra and a second terminal end of the plate contacts the second cut end of the vertebra.

The method can include, after attaching the lamina plate to the first and second screws, attaching at least one receiver head to the lamina plate. Attaching the lamina plate to the first and second screws can include moving the lamina plate from a first compressed position to a second expanded position in which the plate engages the screws.

The present invention further provides devices and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1:
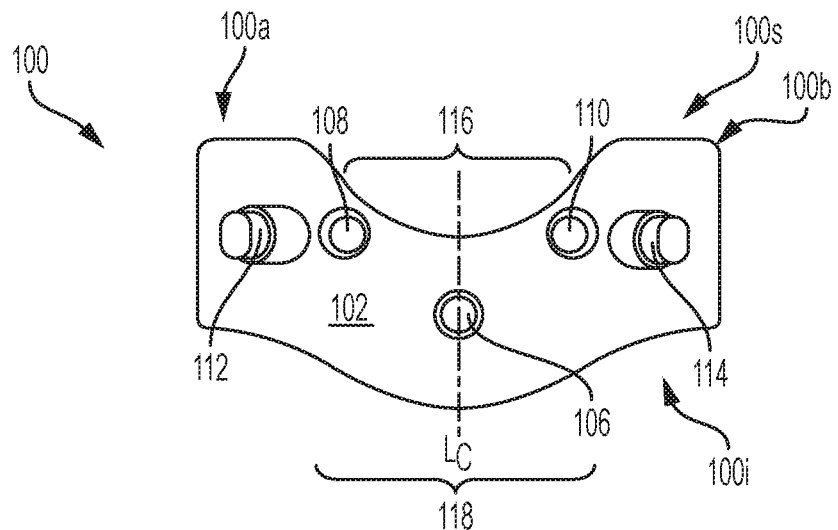
FIG. 1 is a posterior view of a lamina plate.

Devices, systems, and methods for reducing trauma from spinal stabilization and/or decompression procedures are described herein. Lamina prosthesis plates are provided herein and are configured to be positioned on a vertebra following a laminectomy procedure. In general, a lamina plate can include various features that allow a surgeon to couple the plate to a vertebra, such as a plurality of receiving holes for receiving a spinal fixation element (e.g. a bone screw). The plate can be shaped and the receiving holes positioned such that the spinal fixation elements can be installed with reduced exposure of the spine and along a trajectory that mirrors the anatomy of the bone and enhances purchase with the bone, such as a trajectory that allows for longer fixation elements. In certain aspects, the lamina plate can be curved in an anterior direction to provide space for and prevent injury to the spinal cord. The lamina plate can include one or more features for coupling at least one receiver head to the plate for receiving a spinal stabilization element. One or more receiver heads can be selectively positioned on the lamina plate to allow for stabilization (e.g., midline, unilateral, bilateral, etc.) of a patient's spine. Since the receiver heads can be coupled to the plate after the plate is implanted, they do not restrict the range of angles or trajectories at which the spinal fixation elements can be installed. In cases where spinal stabilization is not desired, the features on the lamina plate for selectively coupling to a receiver head need not be used and the lamina plate can be installed as a stand-alone device for replacing laminae and protecting the spinal cord.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Systems and methods herein can provide a number of advantages as compared with traditional decompression and/or fixation solutions. For example, systems and methods herein can facilitate performance of a laminectomy procedure with reduced exposure of the spine and associated patient trauma. Systems and methods herein can also allow for insertion of spinal fixation elements (e.g., bone screws) along trajectories which provide increased bone purchase, reduced risk of pull-out, and reduced risk of errant insertion.

Trans-lamina fixation procedures are disclosed which can allow for a stronger fixation between the fixation assembly and corresponding vertebral bone. Because the trajectory of each of the fixation assembles can be positioned at larger angles from the midline than traditional insertion techniques, resistance to dorsal pull-out is increased and a larger surface area can be engaged by the fixation assembly. In light of the trajectories, the fixation assembly can include a larger (e.g., longer and/or wider) bone anchor element which also contributes to a stronger fixation. Additionally, trans-lamina delivery and positioning significantly reduces the risk of injury because the distal end of the fixation assembly can be angled away from a spinal canal during delivery as opposed to traditional trajectories which are substantially perpendicular to and/or angled toward the spinal canal. Additionally, in utilizing trans-lamina delivery and positioning, the assembly can enter the vertebrae at a trans-lamina entry point which is a substantially shorter distance from a midline of the spinal column as compared to the distance required when utilizing a traditional direct delivery approach. Thus, the amount of lateral exposure required can be significantly reduced as compared to the traditional approach.

FIG. 1 shows an exemplary embodiment of an implant for a vertebra, e.g., a cervical vertebra, generally referred to herein as a lamina plate 100. The body of the plate 100 can have a posterior surface 102 configured to face away from a patient's spine when the plate is implanted and an anterior surface 104, shown in FIGS. 2A and 2B, configured to face towards and be positioned adjacent to a patient's spinal canal when the plate is implanted. The plate 100 can also include a superior surface 100s and an inferior surface 100i, as well as opposed first and second lateral ends 100a, 100b. The plate 100 can include one or more features formed therein for mating with a receiver head (not shown), such as a first central hole 106 positioned along a central superior-inferior axis $L_c$ of the plate 100 and first and second lateral holes 108, 110 disposed laterally offset from the central superior-inferior axis $L_c$. As discussed in greater detail below, these features can allow a user to selectively position one or more receiver heads on the lamina plate 100. The plate 100 can further include one or more fixation element receiving holes, such as receiving holes 112, 114, that can receive a spinal fixation element to couple the plate 100 to a vertebra.

The plate can have various sizes, shapes, and configurations. The anterior and posterior surfaces of the plate can be shaped in various ways, such as rectangular, square, elliptical, or circular shaped, etc. In certain aspects, the plate can be sized and shaped to facilitate positioning of multiple plates on the lamina of adjacent vertebrae. As shown in FIG. 1, the superior surface 100s of the plate 100 can have a concave, curved portion 116 and the inferior surface 100i of the plate 100 can have a convex, curved portion 118. The concave portion 116 can substantially correspond to the convex portion 118. For example, a radius of curvature of the concave portion 116 can be substantially equal to a radius of curvature of the convex portion 118. The shape and degree of the curvature of the concave and convex portions 116, 118 can vary and by way of non-limiting example, can have a compound curve, parabolic curve, etc. In general, having a concave portion 116 that corresponds to the convex portion 118 in size, shape, and degree of curvature can allow lamina plates to be positioned on adjacent vertebrae without interfering with and contacting one another during bending, twisting, or other movement of the spine. The concave portion 116 can also form a relief in which a spinous process of an adjacent superior vertebra can be positioned so that the spinous process does not restrict movement of the spine such as by being pressed against the lamina plate. The radius of curvature of the concave and convex portions 116, 118 can vary. For example, the radius of curvature of the concave portion 116 can be in the range of about 1 to about 15 mm and the radius of curvature of the convex portion 118 can be in the range of about 1 to about 20 mm. In certain aspects, the radius of curvature of the concave and convex portions 116, 118 can be substantially equal.

As will be appreciated, a height of the plate 100 can vary in a horizontal direction. For example, a distance between the superior and inferior surfaces 100s, 100i can be substantially equal, moving horizontally from the first lateral end 100a to the second lateral end 100b of the plate 100, as shown, or a distance between the superior and inferior surfaces can vary. In the illustrated embodiment, a distance between the superior and inferior surfaces 100s, 100i can be in the range of about 18 to about 20 mm.

Figure 2A:
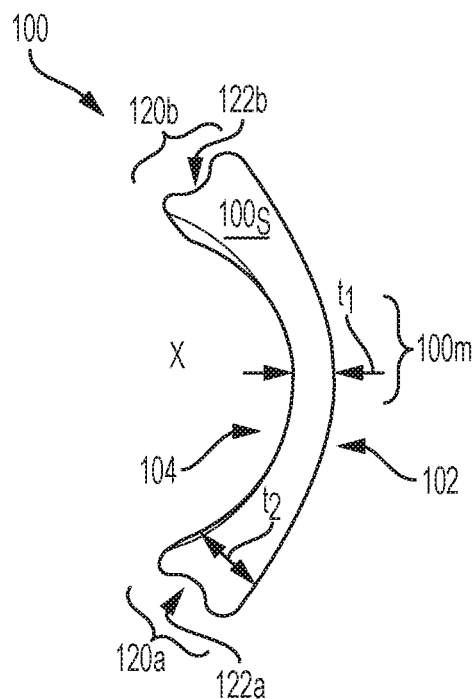
FIG. 2A is a superior view of the lamina plate of FIG. 1.
Figure 2B:
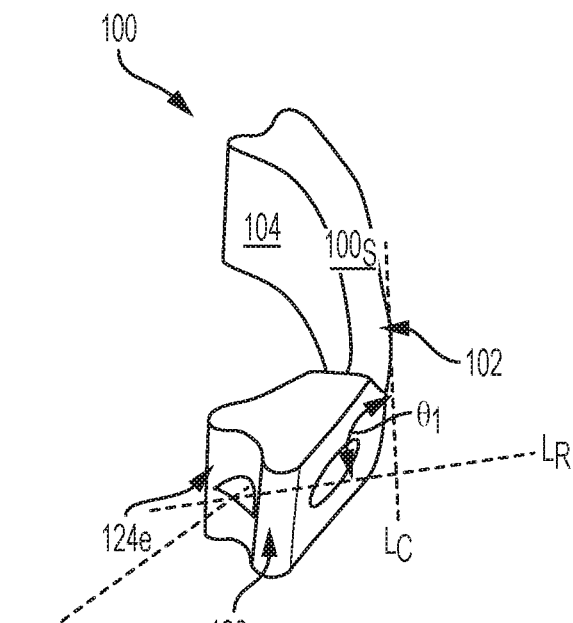
FIG. 2B is a perspective view of the lamina plate of FIG. 1.

The plate can have a curve X, as best shown in FIGS. 2A-2B, which can be formed about the central superior-inferior axis $L_c$ such that the anterior surface of the body defines a curved relief configured to be disposed over a patient's spinal cord when the plate is implanted. More specifically, the plate 100 can be curved about the central superior-inferior axis $L_c$ such that the opposed lateral ends 100a, 100b of the plate are positioned anterior to a mid-portion of the plate 100. As a result, the posterior face 102 of the plate 100 can have a substantially convex shape about the central superior-inferior axis $L_c$. The anterior face 104 of the plate 100 can have a substantially concave shape about the central superior-inferior axis $L_c$ that can be substantially the same in size and degree of curvature as that of the posterior face 102. In general, the curve X can be substantially equal to a curvature of the laminae prior to the laminae being removed from the patient or the curve X can have a greater degree of curvature to allow for more space between the spinal cord and the anterior face 104.

Figure 2C:
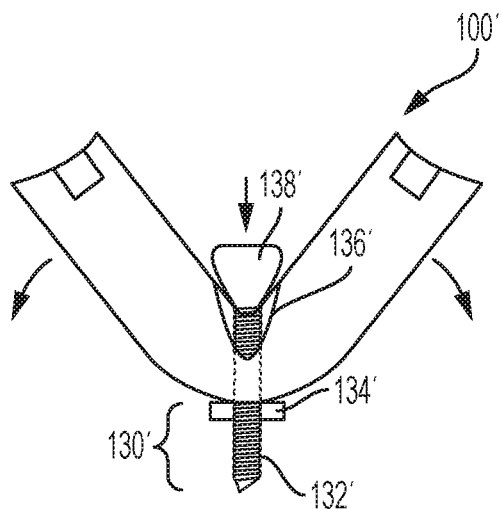
FIG. 2C is a superior view of a lamina plate having an adjustable curvature and being in a first, compressed position.
Figure 2D:
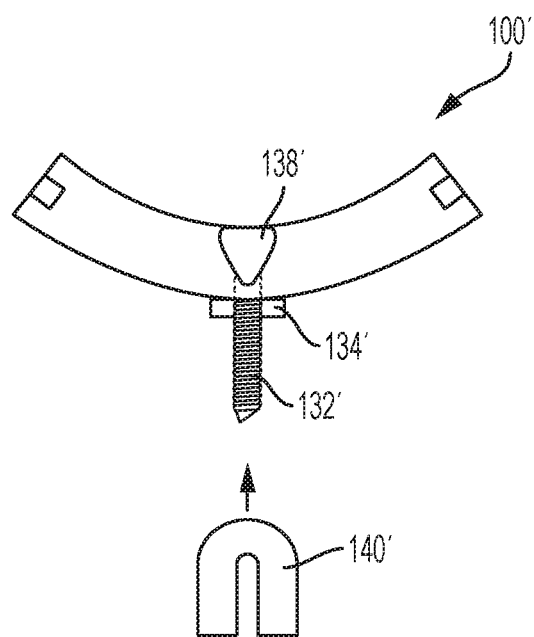
FIG. 2D is superior view of the lamina plate of FIG. 2C in a second, expanded position.

In some embodiments, a lamina plate can have one or more features that allow its curvature to be selectively adjusted by a user, such as a living hinge, spring, etc. For example, FIGS. 2C and 2D illustrate an exemplary lamina plate 100' having an adjustment mechanism 130' for adjusting the degree of curvature of the plate. The illustrated adjustment mechanism 130' includes a threaded rod 132' that extends through the plate in an anterior-posterior direction. A nut 134' is threaded onto the rod 132' adjacent the posterior surface of the plate and an expansion member 138' is coupled to the rod adjacent the anterior surface of the plate. The plate can also include a recess 136' configured to receive at least a portion of the expansion member 138' therein. The plate can be formed from a resilient material (e.g., such that the plate is biased towards the collapsed configuration). In use, a user can selectively expand and compress the plate 100' by tightening or loosening the nut 134'. In particular, the nut 134' can be tightened to wedge the expansion member 138' into the recess 136' and move the plate to the expanded position shown in FIG. 2D. The threaded rod 132' can be configured to couple to a receiver member 140' as shown. Features of the receiver member 140' are explained in greater detail below.

The lamina plate 100 can be configured to mate with a vertebra, e.g., a cervical vertebra, and can act as a prosthesis following a full laminectomy procedure in which both laminae and the spinous process are removed from the vertebra. The lamina plate can have a thickness t, measured as a distance perpendicular to the posterior and anterior faces 102, 104. More specifically, the plate 100 can have a first thickness $t_1$ at the central superior-inferior axis $L_c$ of the plate 100 and a second thickness t2 at the first and second lateral ends 100a, 100b of the plate. The thickness t of the plate 100 can increase from the central superior-inferior axis $L_c$ of the plate 100 to the first and second lateral ends 100a, 100b. This can provide structural support to the plate 100 at the ends so that the plate 100 remains firmly coupled to a vertebra and can provide additional clearance at the mid-portion of the plate for patient anatomy.

The lateral ends 100a, 100b of the plate 100 can include first and second lateral mating features 120a, 120b that can be coupled to a vertebra at various locations, such as to a portion of a lamina that remains on the vertebra and/or to a pedicle. The first and second lateral mating features 120a, 120b can be sized, shaped, and contoured in various ways to facilitate contact between the plate 100 and a vertebra. As shown in FIGS. 2A and 2B, the first and second lateral mating features 120a, 120b can have a semi-cylindrical or semi-spherical depression 122a, 122b, the depressions 122a, 122b having a radius of curvature in the range of about 0.5 to about 4 mm. The depressions 122a, 122b can define first and second extension portions 124e, 126e, as best shown in FIG. 2B, that can increase a bone surface area contacted by the plate 100. This can help prevent the plate 100 from shifting in an anterior-posterior direction or any other direction when the implant 100 is coupled to a vertebra. As will be appreciated, the lateral mating features 120a, 120b can have other configurations and, for example, can include a notch, slit, teeth, etc. that can fixedly engage a vertebra.

The lamina plate 100 can include various features for receiving fixation elements that can help maintain the plate 100 in fixed contact with vertebral bone. Referring back to FIG. 1, the lamina plate 100 can have a first receiving hole 112 and a second receiving hole 114, each of the first and second receiving holes 112, 114 being configured to receive a fixation element therein, e.g., a bone screw. As will be appreciated by those skilled in the art, the plate can have any number of receiving holes, such as two receiving holes positioned on the first lateral end of the plate and two receiving holes positioned on the second lateral end of the plate. An axis of the receiving holes 112, 114 can be oriented in various directions relative to the plate 100 so that when a fixation element is inserted therethrough, the fixation element penetrates into a vertebra, such as into the lateral mass (L.M.) of a vertebra. An angle $\theta_1$ between a central axis LR extending through each of the receiving holes 112, 114 and a central ventral-dorsal axis of the implant can be in the range of about 20 to about 70 degrees, and preferably in the range of about 30 to about 50 degrees.

Figure 3:
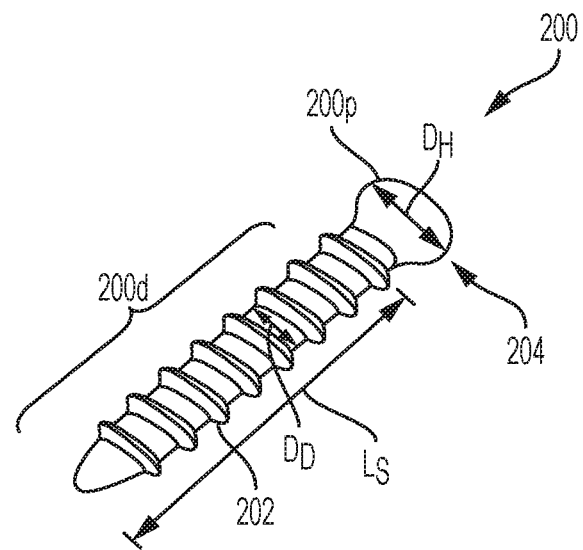
FIG. 3 is a perspective view of an exemplary bone screw for use with a lamina plate.

Fixation element(s) for use with the lamina plate can be virtually any type of element having a distal portion configured to engage vertebral bone. For example, FIG. 3 illustrates a bone screw 200 configured to engage vertebral bone. In an exemplary embodiment, the bone screw 200 has one or more threads 202 extending along a distal portion 200d thereof, the threads 202 allowing the screw 200 to be effectively delivered to and securely positioned within a vertebra. A proximal portion 200p of the screw 200 can include a head 204 that can have one or more engagement features (not shown) that can mate with an insertion tool for driving the screw 200 through the plate 200 and into bone. While the fixation element can include a wide range of sizes and/or shapes, as indicated above, an advantage of translamina delivery is the ability to utilize longer elements compared to a traditional approach where tissue is cut and/or retracted between a midline of the vertebra and the lateral mass and a bone screw is inserted so that it extends directly into the lateral mass of a vertebra. For example, FIG. 3 shows an embodiment of a bone screw 200 having a length $L_S$ that is substantially greater than a length of a bone screw utilized in the traditional insertion technique where an additional portion of muscle and tissue must be extracted. The length $L_S$ can be in the range of about 8 to about 25 mm. A diameter $D_D$ of the distal portion 200d of the screw 200 can be in the range of about 1.5 to about 4.0 mm, while a diameter $D_H$ of the head 204 can be in the range of about 2.0 to about 6.0 mm. In some embodiments the maximum outer diameter of the head 204 can be less than or equal to the maximum outside diameter of the distal portion 200d of the screw.

Figure 4A:
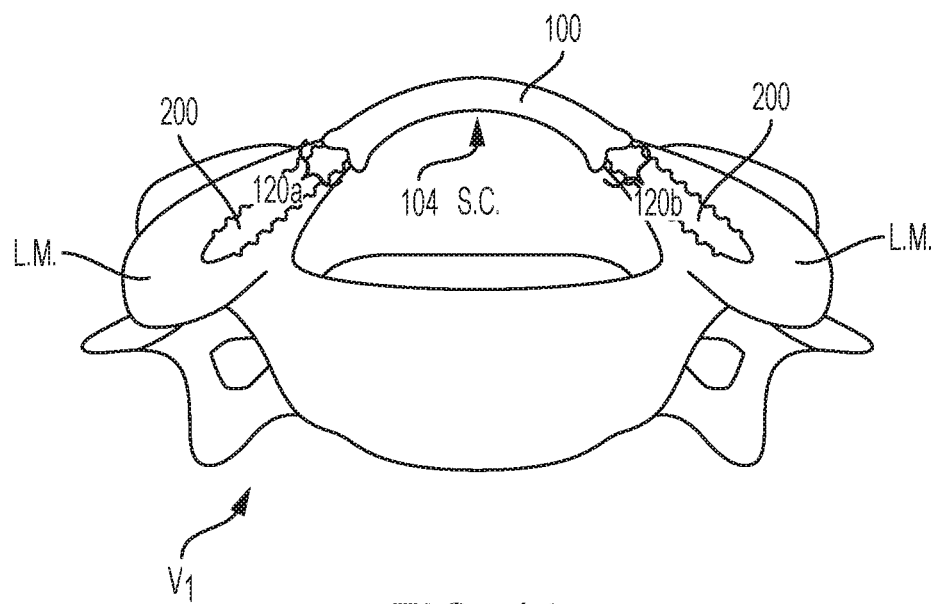
FIG. 4A is a superior view of a lamina plate having two fixation elements extending therethrough to couple the plate to a vertebra.

In use, the lamina plate 100 can be coupled to a vertebra V1 and can act as a prosthesis for first and second laminae, as shown in FIG. 4A. The first and second lateral mating features 120a, 120b can engage with the vertebra V1 and can be secured thereto via first and second screws 200 each extending into a lateral mass (L.M.). The anterior surface 104 of the plate 100 can provide space for the spinal cord, dura, and other anatomy disposed in the spinal canal (S.C.).

Figure 4B:
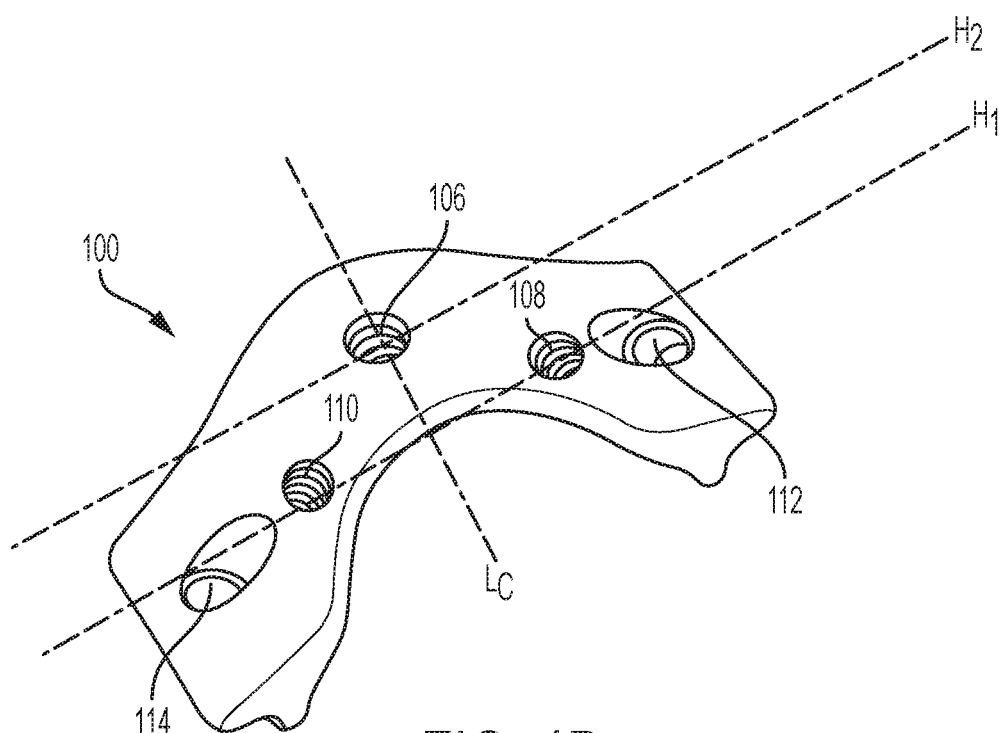
FIG. 4B is a perspective posterior view of a lamina plate having a plurality of mating features for mating with a receiver head.

The lamina plate can include one or more features, such as one or more recesses or holes referred to herein as receiving features, for selectively and/or removably mating with a receiver head for allowing fixation of the spine. As will be appreciated, a lamina plate can have any number of receiving features formed therein, such as zero, one, two, three, four, five, etc., positioned at various locations on the plate. As shown in FIG. 4B, the lamina plate 100 can include three receiving features, including a first, central receiving feature 106 positioned along the central superior-inferior axis $L_C$ of the plate 100 and first and second lateral receiving features 108, 110 positioned lateral to the first, central receiving feature 106. The first and second lateral receiving features 108, 110 can be positioned along a longitudinal, horizontal axis of the plate $H_1$ that is offset from a longitudinal, horizontal axis $H_2$ extending through the first, central receiving feature 106. That is, the first central receiving feature 106 can be positioned inferior to the first and second lateral receiving features 108, 110. The first and second lateral receiving features 108, 110 can be positioned on opposite sides of the central superior-inferior axis $L_C$, as in the illustrated embodiment, to allow for bilateral stabilization. As will be appreciated, receiving features can be positioned in various other ways along the plate, such as the central receiving feature 106 being positioned superior to the first and second lateral receiving features 108, 110. Each of the receiving features 106, 108, 110 can be holes formed through the posterior and anterior surfaces 102, 104 of the plate 100, substantially perpendicular to said surfaces 102, 104 or at an oblique angle to said surfaces 102, 104. In some embodiments, one or more of the receiving features can be depressions that do not extend through the anterior surface of the plate. The receiving features can include various features that facilitate engagement with a receiver head, such as one or more threads extending along an inner surface thereof, as shown in FIG. 4B. As described further below, the receiver head 300 can include a threaded feature, such as a screw 308, configured to mate with the internal threads in the receiving feature.

Figure 5A:
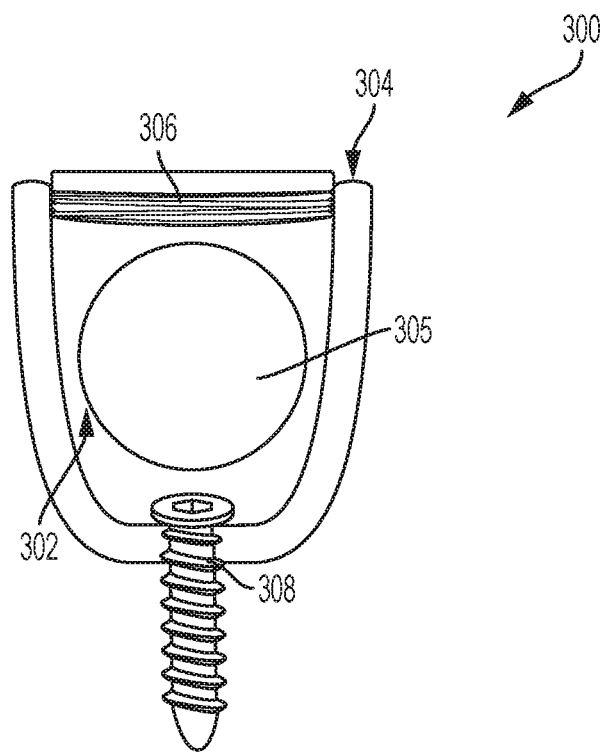
FIG. 5A is a perspective view of an exemplary receiver head.

A lamina plate can be configured in various manners to securely engage a spinal stabilization element (e.g., a rigid or flexible stabilization rod, tether, or tape). For example, a receiver head can be coupled to the lamina plate at any number of locations, such as in any of the receiving features formed in the plate. Such a receiver head can be configured to securely receive the spinal stabilization element in various manners. For example, in an exemplary embodiment shown in FIG. 5A, a receiver head 300 can include a "U"-shaped opening 302 configured to receive a stabilization element 305. In other embodiments, the opening 302 can be shaped in other ways such that the opening 302 is capable of receiving a stabilization element. A receiver head can also be configured in various manners so as to secure the stabilization element therein. For example, the receiver head can include various internal threads 304 around an inner circumference thereof and capable of receiving a closure mechanism, such as locking cap 306 or set screw, thereby securing the stabilization element 305 within the head 300. Alternatively, or in addition, the receiver head can include external threads and a locking nut. Those skilled in the art will appreciate that the receiver head can be configured in various manners so as to retain a stabilization element therein.

Figure 5B:
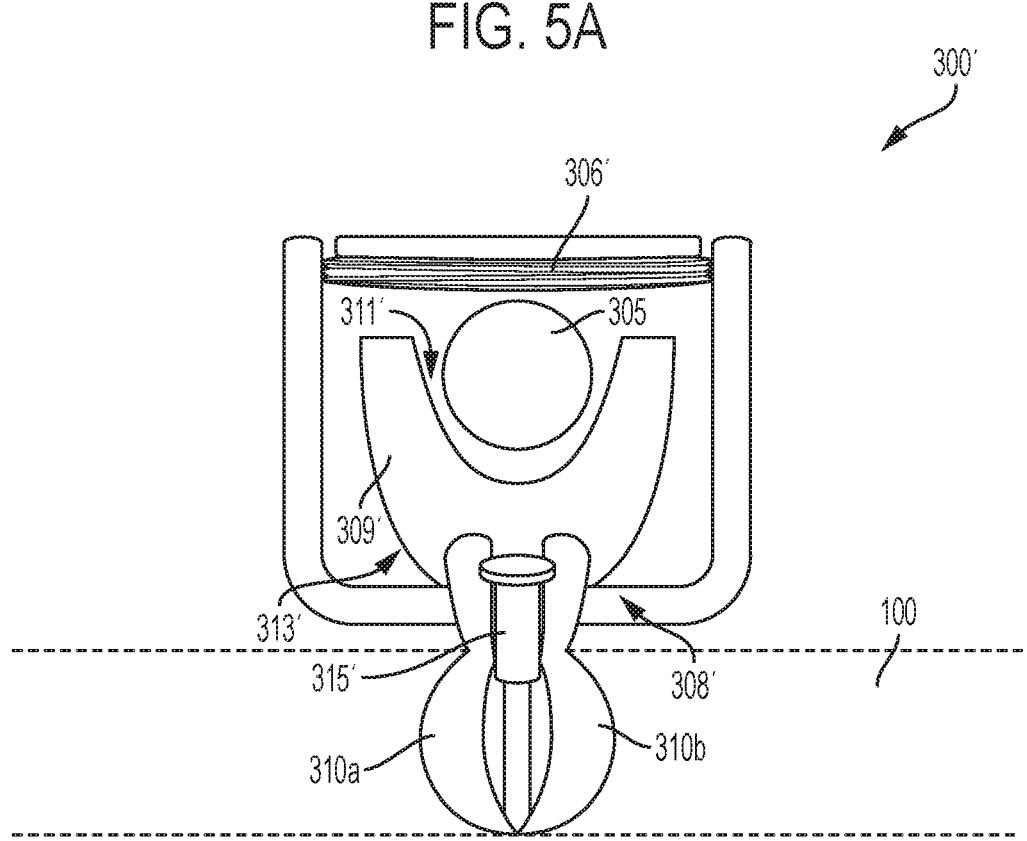
FIG. 5B is a perspective view of another exemplary receiver head.
Figure 6A:
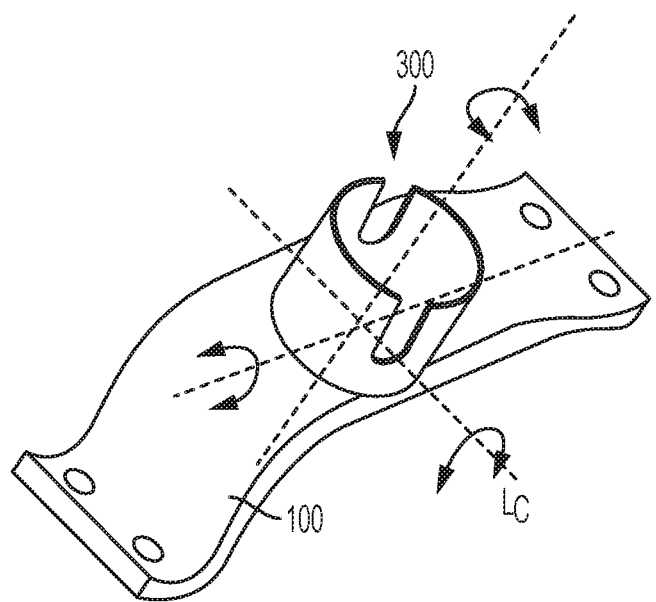
FIG. 6A is a perspective view of a single receiver head coupled to a lamina plate.
Figure 6B:
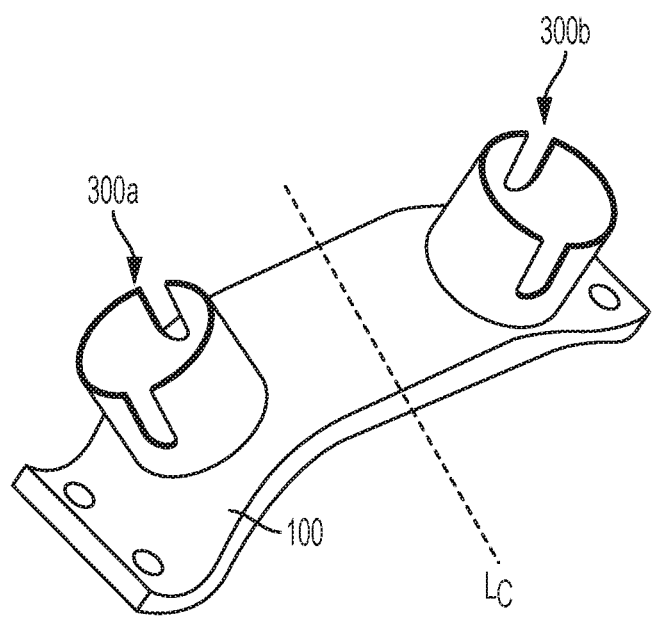
FIG. 6B is a perspective view of first and second receiver heads coupled to a lamina plate.

The systems herein can be configured to allow for movement of a receiver head relative to the lamina plate, such as pivoting of a receiver head relative to the plate to allow stabilization of complex spinal deformities. While a receiver head can be coupled to a lamina plate in any number of ways to provide any desired movement and/or range of motion, in an exemplary embodiment, the receiver head is capable of polyaxial movement relative to the plate. It will be appreciated that the receiver head can be configured and/or coupled in various such manners so as to provide such polyaxial motion. For example, the receiver head can include a spherical portion that is seated or captured in a spherical seat formed in the plate. In some embodiments, the receiver head can be selectively rotated relative to the lamina plate when it is coupled to the plate, thereby allowing for the openings of the various receiver heads to be aligned relative to one another prior to delivery of the stabilization element therethrough. In some embodiments, the receiver head can be uniplanar (configured to pivot along a single plane) or monoaxial (axially fixed relative to the plate with no ability to pivot relative to the plate). In the embodiment shown in FIG. 5B, the act of securing a closure mechanism 306' within the receiver head 300' can lock the head 300' relative to the plate 100 at the current angular position. This can be achieved, for example, via an expandable anchor element 308' extending through the receiver head 300' and into the plate 100, the anchor element 308' having one or more arms, such as first and second arms 310a, 310b that move radially outward similar to a drywall anchor, when the stabilization element 305 is locked in the head 300'. That is, as the closure mechanism 306' is rotated, a lower surface thereof contacts the stabilization element 305. This moves the stabilization element 305 downward within the receiver head 300' toward a cradle 309'. The cradle 309' can have an upper surface 311' that seats the stabilization element 305 therein and a lower surface 313' coupled to the anchor element 308' such that when the stabilization element 305 is seated in the upper surface 311' of the cradle 309', a pin 315' is driven distally between the arms to cause the arms expand radially outward and lock the head 300' in the plate. While the receiver heads can be disposed at various locations, as shown in FIG. 6A, a single receiver head 300 can be positioned in the first, central mating feature along the central superior-inferior axis $L_C$ of the lamina plate 100. In another embodiment, as shown in FIG. 6B, first and second receiver heads 300a, 300b can be positioned in the first and second lateral mating features, respectively, on opposed sides of the central superior-inferior axis $L_C$.

One or more stabilization elements (e.g., stabilization rods) can be secured to the receiver heads in the lamina plate to provide the desired therapeutic effect. The stabilization element can be a rigid or flexible rod, a tether, a tape, a cable, a biological construct, etc. The stabilization element can have a wide range of dimensions (e.g., length and/or diameter) and/or shapes (e.g., straight, contoured, etc.) which are selected in accordance with the patient's anatomy and/or the requirements of the surgical procedure. As also shown, exemplary methods can include positioning first and second stabilization elements on opposite sides of the midline (M.L.) of the patient's spinal column or can include positioning a single stabilization element along and above the midline (M.L.) of a patient's spinal column. The lamina plate and spinal fixation assemblies can be configured to receive a variety of fixation elements. Suitable spinal stabilization elements include, by way of non-limiting examples, rods, tethers, cables, plates, etc. The spinal stabilization elements can have a variety of configurations, and, by way of non-limiting example, can be rigid, semi-rigid, bendable, flexible, etc. The spinal stabilization elements can include additional features which improve the integration of the system within the patient's body. For example, in some embodiments, the spinal stabilization element can additionally include a fin to which soft tissue can be attached to promote integration and post-surgical recovery, as discussed further below.

In an exemplary embodiment, the spinal stabilization element is an elongate rod. While the rod can be substantially straight, the rod can also be bent or curved in one or more dimensions to allow the rod to extend across multiple vertebrae. The bend or curve can take any shape, but it can be preferable for the rod to be complementary to a curve of the spine. Thus, the shape of the rod can be substantially similar to a natural curve of the spine or a desired post-surgical curve of the spine along the midline (M.L.). For example, the rod can be curved to extend from the spinous process of one vertebra to the spinous process of an adjacent vertebra, while maintaining a close association with the contours of the spinal column therebetween. In some instances, the curve of the rod can be pre-determined. In other instances, the rod can include some flexibility to allow the rod to be shaped in accord with its implant location. In even other instances, the rod can be fully bendable so it can be formed into any desired shape along its length. The rod can also be curved or branched in one or more planes (e.g., in a coronal plane) to extend, e.g., from a midline of cervical vertebrae to lateral side(s) of thoracic vertebrae or other inferior vertebrae. The rod can also have a variety of cross-sections. For example, the rod can have a circular cross-section. Alternatively, rods for use on the midline of the spine can also be shaped so as to provide increased torsional stability. For example, in one embodiment, the rod can have an irregular and/or rectangular cross-section.

Figure 7A:
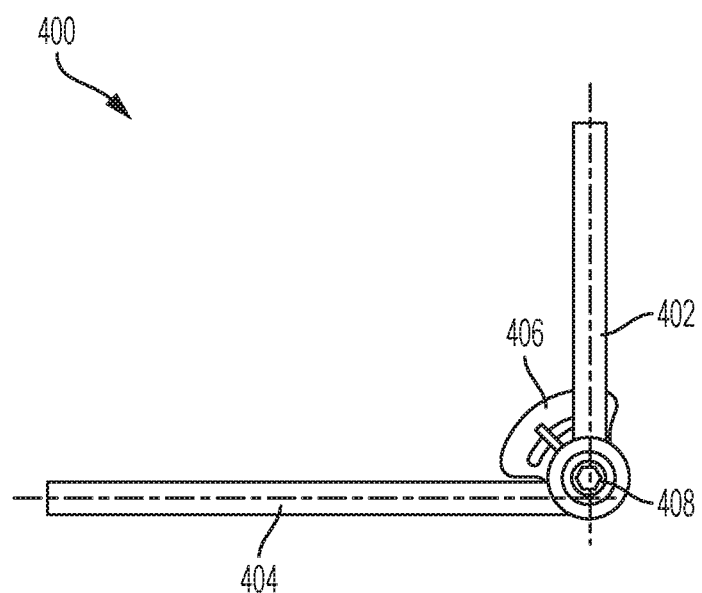
FIG. 7A is a perspective view of an adjustable-angle spinal rod assembly with an angle gauge.
Figure 7B:
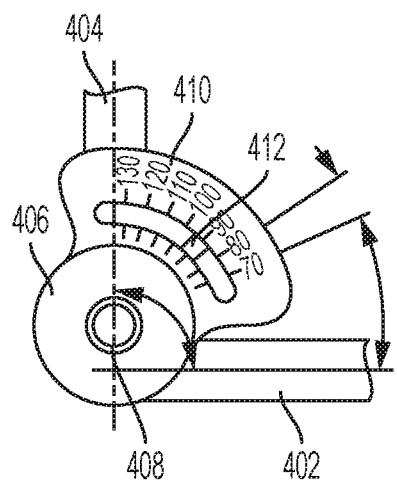
FIG. 7B is a side view of the assembly of FIG. 7A.
Figure 7C:
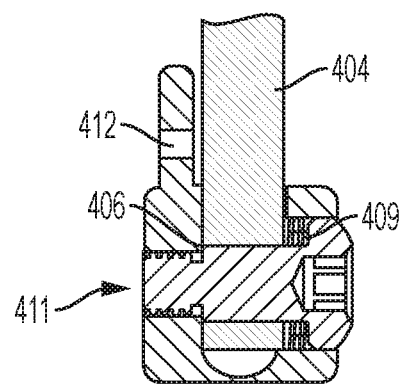
FIG. 7C is a side, sectional view of the assembly of FIG. 7A.

In some embodiments, an adjustable-angle spinal rod assembly can be used. The assembly can include first and second rods coupled to one another at a rotation joint such that an angle between the first and second rods can be adjusted. In some embodiments, the assembly can include an angle gauge that can help a surgeon set the first and second rods to a desired angular relationship. While use of such an assembly is disclosed herein primarily in relation to fixation procedures that involve lamina plates, the assembly can also be used in other procedures such as occipital-cervical fixation procedures using traditional pedicle screws. As shown in FIG. 7A, an adjustable-angle spinal rod assembly 400 can generally include first and second elongate arms 402, 404 pivotably coupled to one another at a pivot point 408. One of the first and second arms 402, 404 can include an angle gauge 406 formed integrally therewith or coupled thereto. As shown in FIG. 7B, the angle gauge 406 can include a plurality of markings 410 in degrees or other units and can include an indicator 412 that moves as the angle between the first and second arms 402, 404 is adjusted, the gauge 406 being calibrated such that the indicator 412 is aligned with the marking that corresponds to the current angle between the first and second arms 402, 404. In some embodiments, the angle gauge 406, including the indicator 412, can be removable from the first and second arms 402, 404. In use, the assembly 400 can be inserted into a patient and the arms 402, 404 can be coupled to receiving elements attached to the patient's spine. The patient's spine can then be adjusted to a desired angle, as indicated by the angle gauge, at which point a locking member or screw 409 (shown in FIG. 7C) can be tightened within an opening 411 to lock the assembly to the desired angle and thereby fix the patient's spine at said angle. Alternatively, or in addition, the assembly can be used as a measurement tool to provide a surgeon with an estimate as to the angles between various receiver heads across multiple levels of a spine.

Figure 8:
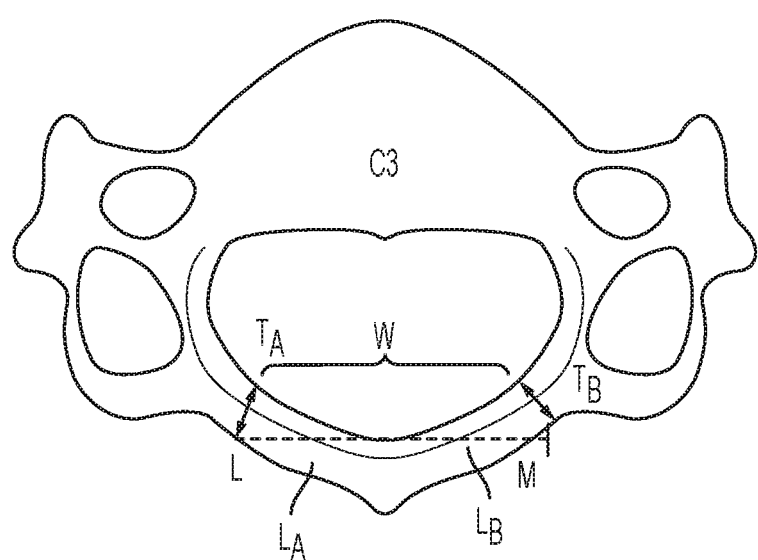
FIG. 8 is a superior view of a vertebra, including a thickness of a lamina following a laminectomy procedure.

In addition to the various systems and devices for spinal decompression and/or stabilization described above, methods for providing spinal decompression and/or stabilization are also described herein. An exemplary method for decompressing a vertebra can include removal of both first and second laminae of the vertebra, commonly referred to as a full laminectomy procedure. A full laminectomy can be performed on a single vertebra, on consecutive/adjacent vertebrae, on alternating vertebrae, etc., as desired. An exemplary laminectomy procedure on a cervical vertebra is shown in FIG. 8, which shows a horizontal width W from a first cut L to a second cut M in first and second laminae $L_A$, $L_B$ as well as resulting first and second thicknesses $T_A$, $T_B$ at the cut portions. The horizontal width W can be in the range of about 15 to about 30 mm, and the first and second thicknesses can be in the range of about 2 to about 8 mm.

The first and second thicknesses $T_A$, $T_B$ of the cut portions can be less than or equal to the thicknesses of the first and second lateral mating features 120a, 120b of the lamina plate 100 to facilitate coupling the lamina plate 100 to the vertebra. For a thoracic vertebra, the horizontal width W can be in the range of about 10 to about 20 mm. For a lumbar vertebra, the horizontal width W can be in the range of about 10 to about 35 mm. For the cervical, thoracic, and the lumbar vertebrae, the first and second thicknesses $T_A$, $T_B$ can be in the range of about 2 to 8 about mm.

Figure 9A:
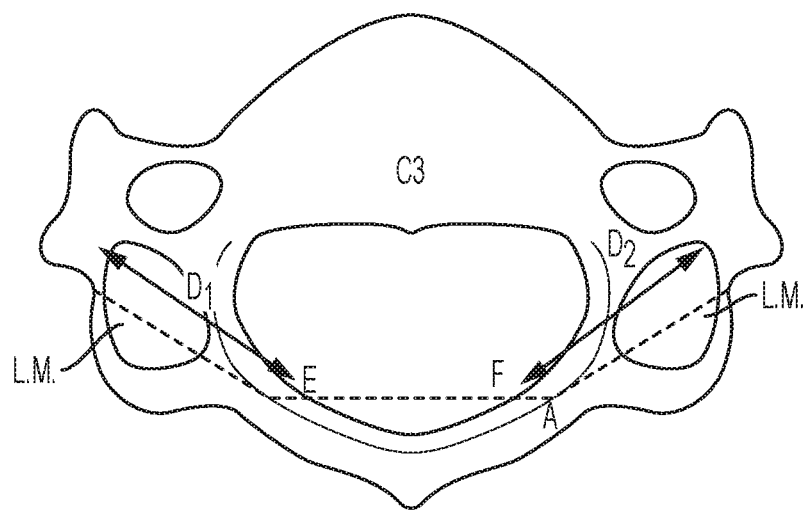
FIG. 9A is a superior view of a vertebra, including distances to an anterior end of first and second lateral masses.
Figure 9B:
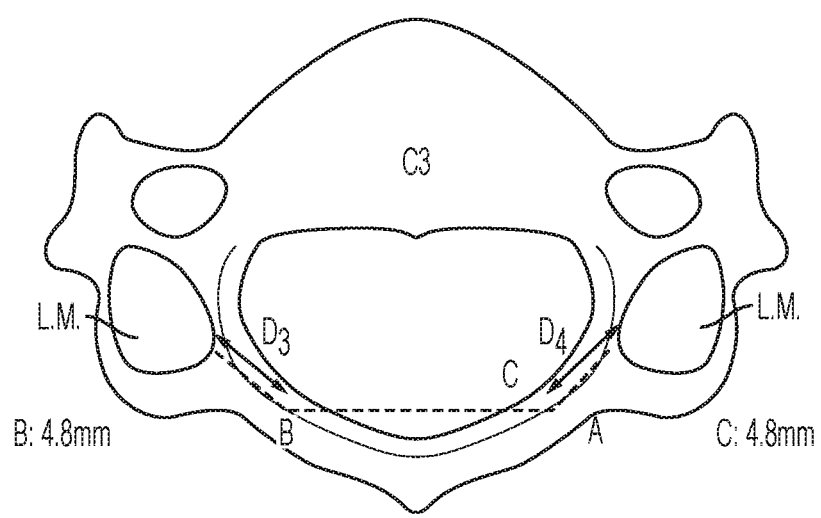
FIG. 9B is a superior view of the vertebra of FIG. 9A, including distances that approximate a portion of each lamina that will remain after a full laminectomy is performed.

A length of fixation elements that couple a lamina plate to a vertebra can be selected based on a size and shape of the vertebra. FIGS. 9A and 9B illustrate distances to various regions of a cervical vertebra $C_3$. FIG. 9A illustrates first and second distances $D_1$, $D_2$ from first and second cut portions E, F to an outer or anterior edge of first and second lateral masses (L.M.), respectively, which can be in the range of about 10 to about 20 mm. FIG. 9B illustrates first and second distances $D_3$, $D_4$ representing the length of the remaining lamina when the laminae are cut at first and second cut portions A, B. The distances $D_3$, $D_4$ can be in the range of about 0 to about 8 mm. For a thoracic vertebra, the first and second distances $D_1$, $D_2$ can be in the range of about 15 to about 22 mm and the first and second distances $D_3$, $D_4$ can be in the range of about 0 to about 5 mm. For a lumbar vertebra, the first and second distances $D_1$, $D_2$ can be in the range of about 15 to about 30 mm and the first and second distances $D_3$, $D_4$ can be in the range of about 0 to about 10 mm.

Figure 10:
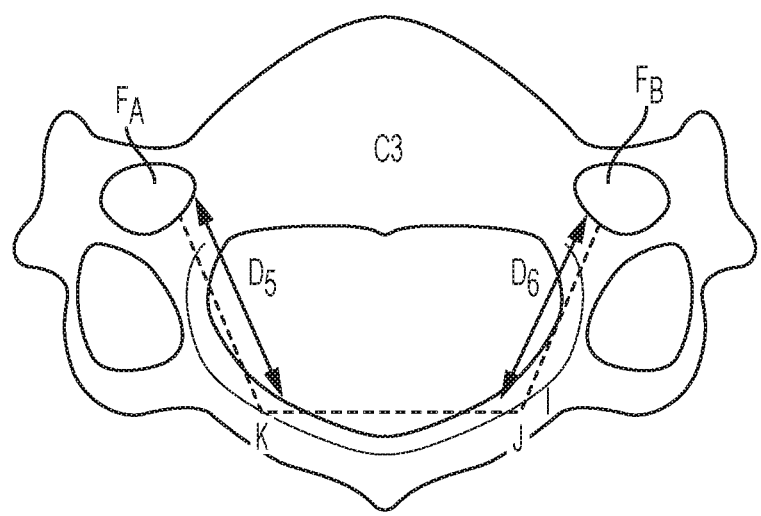
FIG. 10 is a superior view of the vertebra of FIG. 9A, including distances to first and second foramen.

FIG. 10 illustrates first and second distances $D_5$, $D_6$ from cut portions K, J to first and second foramen, $F_A$, $F_B$, respectively, which can be in the range of about 10 to about 20 mm. Based on these measurements, a fixation element, e.g., a bone screw, used to affix the lamina plate 100 to a cervical vertebra can have a distal bone-engaging portion having a length in the range of about 10 to about 20 mm and a width in the range of about 2 to about 8 mm. For a fixation element that penetrates into a thoracic vertebra, which does not have a lateral mass, the fixation element can have a distal bone-engaging portion having a length in the range of about 15 to about 22 mm. For a fixation element that penetrates into a lumbar vertebra, which also does not have a lateral mass, the fixation element can have a distal bone-engaging portion having a length in the range of about 15 to about 30 mm.

Figure 11A:
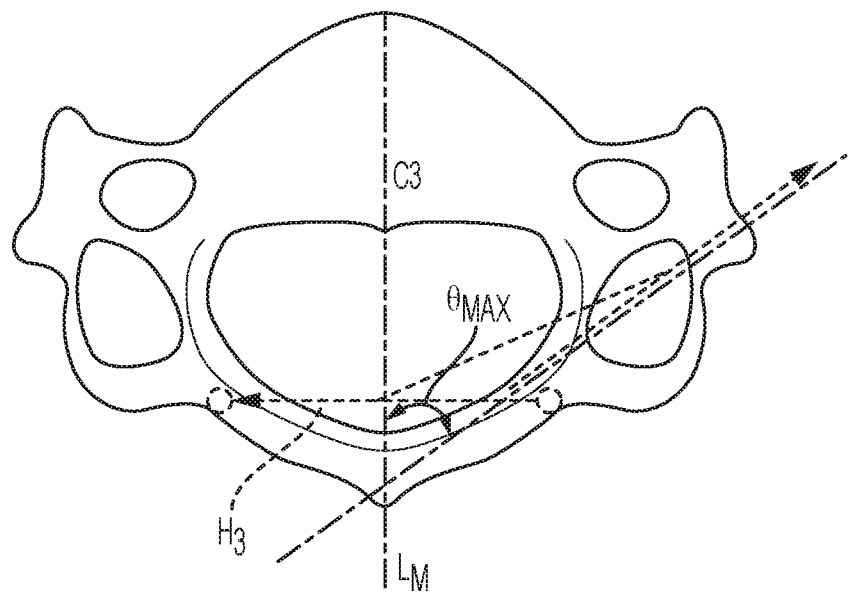
FIG. 11A is a superior view of a vertebra, including an angle of entry of a bone screw into the lateral mass.
Figure 11B:
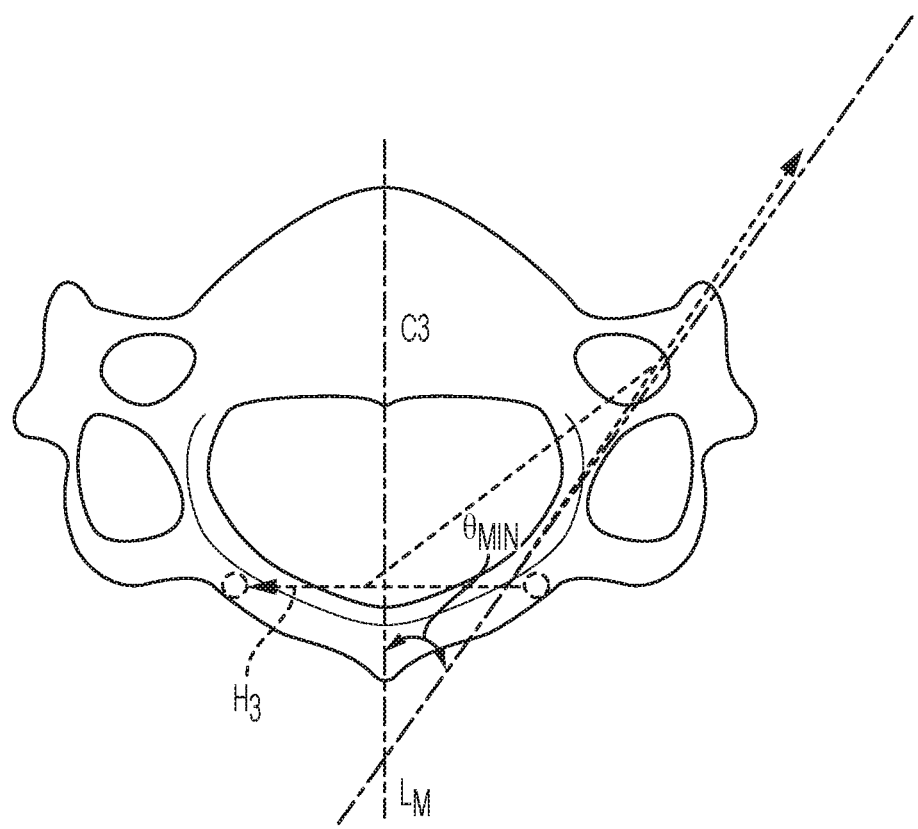
FIG. 11B is a superior view of the vertebra of FIG. 11A, including an angle of entry of a bone screw toward the foramen.

A trajectory of a fixation element into a lateral mass (L.M.) of a cervical vertebra $C_3$ is shown in FIGS. 11A-11B. This angle of entry can be defined relative to a midline $L_M$ of the vertebra. A horizontal axis $H_3$ is also shown extending between first and second laminae, approximately at the portions that will be cut from the vertebra $C_3$ to decompress the vertebra $C_3$ and receive a lamina plate. As shown in FIG. 11A, a trajectory of a fixation element can extend through the pedicle and into a central portion of the lateral mass and can be at an angle $\theta_{MAX}$ of about 60 degrees relative to the midline $L_M$ of the vertebra. As shown in FIG. 11B, a trajectory of a fixation element can be oriented toward a lateral edge of a foramen and can define a minimum angle $\theta_{MIN}$ for the fixation element, the angle $\theta_{MIN}$ being about 40 degrees relative to the midline $L_M$ of the vertebra. For thoracic and lumbar vertebrae, the trajectory of the fixation element can be at an angle $\theta_{MIN}$ to $\theta_{MAX}$ in the range of about 20 degrees to about 70 degrees. It will be appreciated that $\theta_{MIN}$ to $\theta_{MAX}$ can be greater or less than the non-limiting exemplary values and ranges specified here, based on specific patient anatomy and other factors.

A fixation element can be inserted within these stated ranges of angles such that a distal-most end of the fixation element penetrates into a vertebra, such as a lateral mass of a cervical vertebra, without extending into the nerve root or vertebral artery foramen and/or penetrating through an outer surface of the vertebra. The entry of the fixation element at a cut portion of a lamina following a full laminectomy procedure, in combination with lateral mass penetration, can permit longer screws to be inserted into the vertebra than in traditional insertion techniques. This can improve fixation between the fixation element and the bone and help prevent the fixation element from being pulled out of the bone following a surgical procedure. The use of two or more fixation elements extending through the plate and into the vertebra can also resist pull-out. In addition, the angles at which the fixation elements can be installed, which can extend more laterally than in traditional fixation element placements, can provide increased resistance to pull-out forces acting in a posterior direction.

Figure 12:
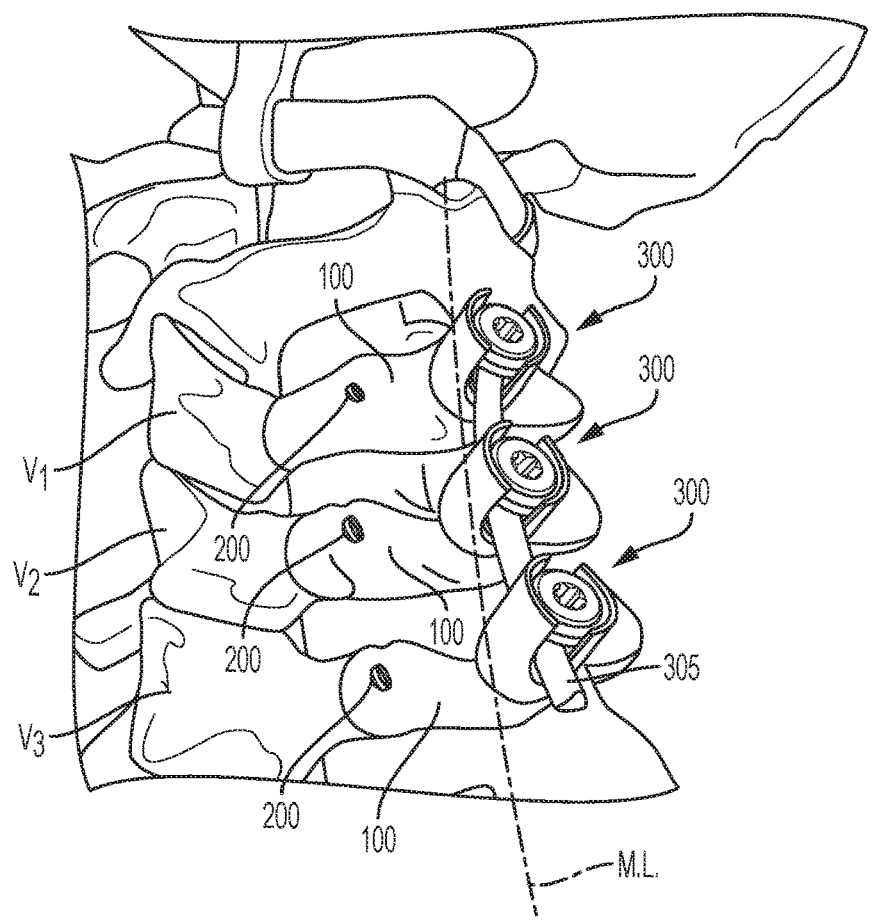
FIG. 12 is a perspective view of a plurality of lamina plates coupled to adjacent vertebrae and having a spinal stabilization element positioned above a midline of the spine.

Referring to FIG. 12, a method for cervical midline fixation can include fixing a plurality of lamina plates of the type described herein to multiple levels of a spine. In particular, a method can include fixing a first lamina plate 100 to a first vertebra $V_1$ of a patient, securing a first receiver head 300 to the first lamina plate 100, fixing a second lamina plate 100 to a second vertebra $V_2$ of a patient, and securing a second receiver head 300 to the second lamina plate 100. Two bone screws 200 can be inserted through each of the lamina plates and into the lateral mass of each vertebra $V_1$, $V_2$, in a trans-lamina trajectory, to secure the lamina plates in fixed engagement with their respective vertebra. In the depicted embodiment, the receiver heads 300 of the lamina plates 100 are positioned so as to be aligned above the midline (M.L.) of the patient's spine. A spinal stabilization element 305 can then be secured to the first and second receiver heads 300 above the midline (M.L.) of the patient's spine. In some embodiments, additional vertebral levels can be included. For example, as also shown in FIG. 12, the method can include fixing a third lamina plate 100 to a third vertebra V3, coupling a third receiver head 300 to the third lamina plate, and securing the stabilization element 305 to the third receiver head. In some embodiments, the method can include securing a receiver head to one or more of the bone screws 200 inserted through the lamina plate. As will be appreciated, the lamina plate need not have receiver head(s) for receiving a stabilization element and can instead be used for replacing the laminae and protecting the spinal cord rather than providing fixation or stabilization across multiple vertebral levels.

The lamina plates can be disposed on consecutive, adjacent vertebral levels of the spine, or alternatively can be coupled to alternating levels of the spine. As previously mentioned, the plates can include a relief formed in a superior surface thereof or can otherwise be sized and shaped to allow plates to be coupled to adjacent vertebrae, if desired, where each vertebra has a full laminectomy procedure performed thereon prior to the plate being coupled thereto. The techniques herein differ from certain existing procedures/prostheses that require single laminectomies on the vertebrae, where a single laminectomy on a first vertebra is performed on a first side of a midline and a single laminectomy on a second, adjacent vertebra is performed on a second side of a midline, and so forth. The techniques herein also differ from traditional procedures/prostheses because the surgeon does not need to remove tissue from or otherwise expose the lateral mass, the lamina plate can be coupled to a vertebra having a full laminectomy, and the lamina plate can act as a protective element for the spinal cord. As indicated above, the presently disclosed methods allow for delivery and positioning of any number of lamina plates to any number and/or pattern of vertebrae. In other embodiments, the method can include any number of lamina plates (e.g., 1, 3, 4, 5, etc.) and any number of receiver heads (e.g., 0, 1, 2, 3, 4, 5, 6, etc.) configured to receive and secure a single or plural spinal stabilization elements of any desired length. Additionally, lamina plates can be secured to sequential vertebra, every other vertebra, every fourth vertebra, or any other pattern required and/or preferred for a given procedure. Such versatility allows the surgeon to select optimal vertebral locations for delivery and positioning of the lamina plates and stabilization elements.

Figure 13:
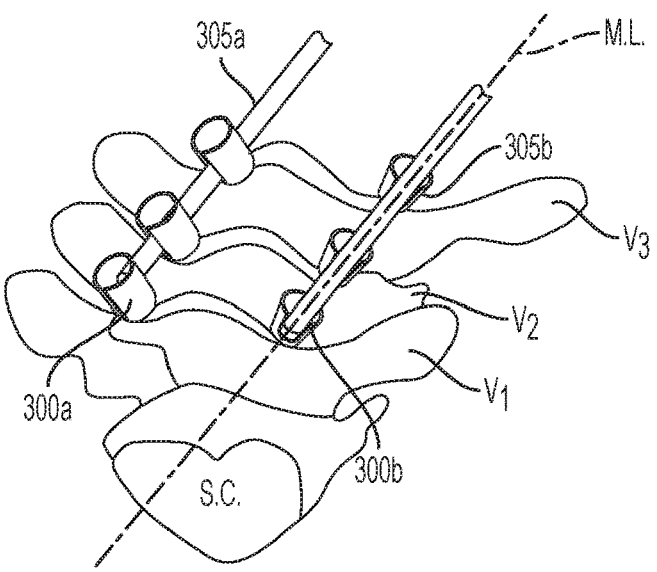
FIG. 13 is a perspective view of a plurality of lamina plates coupled to adjacent vertebrae and having first and second spinal stabilization elements positioned laterally offset from a midline of the spine.

FIG. 13 illustrates an exemplary method in which three lamina plates are secured to consecutive, adjacent vertebra. Each lamina plate 100 can include first and second receiver heads 300a, 300b positioned laterally offset from the midline (M.L.) of the patient's spine, the first receiver head 300a positioned on a first side of the midline (M.L.) of the spine and the second receiver head 300b positioned on a second, opposite side of the midline (M.L.) of the spine. Like the embodiment described above, the lamina plates 100 can be delivered to the vertebrae $V_1$, $V_2$, $V_3$ in various patterns and/or configurations so as to position a plurality of stabilization elements, e.g., two stabilization rods 305a, 305b, in the desired location offset from the midline (M.L.). In some embodiments, similar to what is described above, the lamina plates can be coupled to every other vertebra, every fourth vertebra, etc. In short, the method can include any number of lamina plates positioned within any number and/or pattern of target vertebrae so as to securely position at least one stabilization element in a desired location.

Figure 14A:
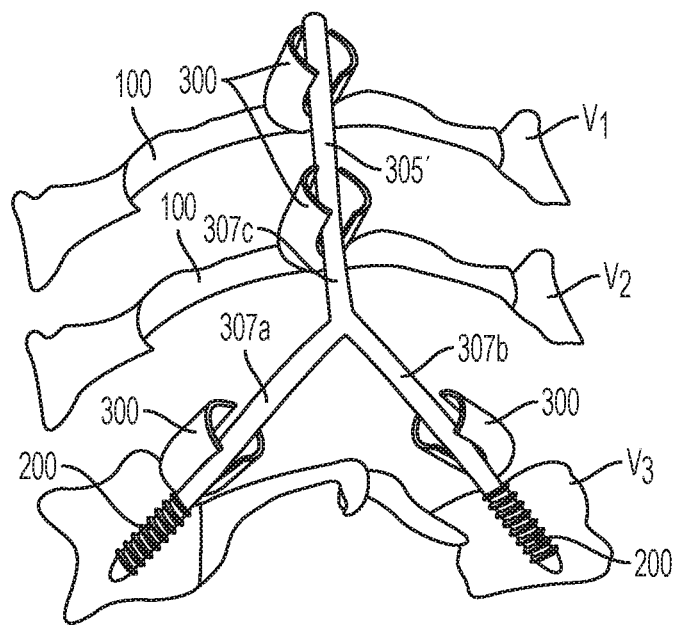
FIG. 14A is a perspective view of a plurality of lamina plates coupled to adjacent vertebrae and having a spinal stabilization element extending above a midline of first and second adjacent vertebrae and having a bifurcated portion being laterally offset from a midline of a third adjacent vertebra.

In another exemplary method shown in FIG. 14A, a bifurcated or branched stabilization element 305' can be used. For example, a stabilization element 305' can be substantially Y-shaped and can have a first arm 307a, a second arm 307b, and a third arm 307c. The first and second arms 307a, 307b can extend at an oblique angle with respect to the third arm 307c. In the illustrate embodiment, the first and second arms 307a, 307b are disposed inferior to the third arm 307c and are secured to a vertebra V3 via first and second pedicle screws 200. The third arm 307c can be secured to one or more vertebrae (e.g., the illustrated vertebrae V1, V2 via respective lamina plates 100. This rod configuration can allow for the rod's position with respect to the spinal column to change from a midline positioning to a lateral or offset positioning along the length of the rod. This flexibility in positioning the receiver heads and for allowing customization of stabilization elements can allow a surgeon to correct complex spinal deformities using the lamina plates herein.

Figure 14B:
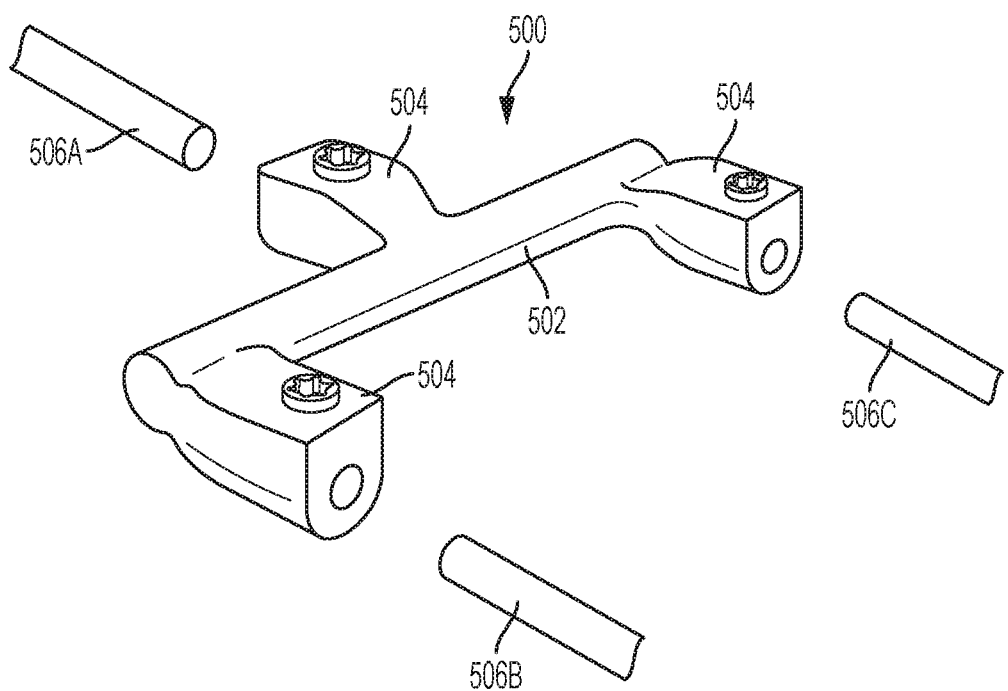
FIG. 14B is a perspective view of a connector that allows a first stabilization element to extend above a midline of one or more vertebrae and second and third stabilization elements to extend above and be laterally offset from a midline of one or more vertebrae.

In another exemplary method shown in FIG. 14B, a connector 500 can be used instead of or in addition to a bifurcated stabilization element. The connector 500 can include a central transverse portion 502 with a plurality of mating features 504 extending therefrom to which spinal rods 506 or other stabilization members can be coupled. While the mating features 504 are shown as female receptacles with locking set screws, it will be appreciated that various other structures for attaching rods to the connector can be used instead or in addition, such as clamps. The illustrated connector 500 has a bifurcated, Y shape which can allow a first stabilization element 506A to be positioned above a midline of one or more vertebrae and second and third stabilization elements 506B, 506C to be positioned lateral to a midline and on opposite sides of the midline of one or more other vertebrae. The stabilization elements 506 can be secured to the vertebrae using lamina plates of the type described herein or using traditional bone anchors. The flexibility in the positioning of receiver heads on the lamina plates as well as the ability to form rod-to-rod connections can also allow a surgeon to correct complex spinal deformities.

Methods for treating one or more vertebrae can include forming one or more incisions in a patient's body and retracting muscle and tissue to access a target vertebra, e.g., a cervical vertebra. A full laminectomy can be performed on the target vertebra such as by forming a first cut at or near a first lamina and a second cut at or near a second contralateral lamina, and removing the first and second laminae from the patient's body. In some embodiments, the distance between the lamina cuts can be in the range of about 15 to about 30 mm and a lateral distance of muscles/tissues retracted to give exposure to the same can be in the range of about 15 to about 40 mm for a cervical vertebra. In general, the degree of exposure of the vertebra for the techniques herein can be less than in traditional procedures where a fixation element is inserted directly into a lateral mass, rather than through a lamina. This can reduce trauma to the patient and facilitate healing because larger incisions and greater dissection in a lateral direction tends to increase a patient's blood loss. Because the size, shape, and curvature of the lamina plate is selected so that the fixation element extends through a lamina, the surgeon need not expose the lateral mass and thus, the degree of exposure is less than in traditional procedures. The cuts formed in the vertebra can be shaved, contoured, or otherwise modified to prepare the cut surface for coupling to a lateral end of a lamina plate.

A lamina plate can be inserted in the patient and positioned in an installed position, e.g., a position in which a first lateral end of the plate contacts and/or receives the first cut portion of the vertebra and a second lateral end of the plate contacts and/or receives the second cut portion of the vertebra such that the plate spans across the first and second cut lamina ends of the vertebra. One or more fixation elements can be inserted through the plate and into the vertebra. For example, a first fixation element, e.g., a bone screw, can be inserted through a first receiving hole in the plate and a second fixation element, e.g., a bone screw, can be inserted through a second receiving hole in the plate. In some embodiments, a distal portion of each of the fixation elements can penetrate into a lateral mass of the vertebra and this can improve fixation strength. The lamina plate need not have a receiver head/stabilization element coupled thereto and can act as a lamina prosthesis that protects the spinal cord without stabilizing the spine. The lack of a receiver head can provide adequate clearance to facilitate insertion of the fixation elements along the trajectories disclosed herein, which minimizes or eliminates the need for additional lateral exposure of the vertebra.

In other embodiments, one or more receiver heads can be coupled to the lamina plate to allow for both stabilization of the spine and protection of the spinal cord. In such embodiments, the receiver head or heads can be coupled to the lamina plate prior to inserting the lamina plate into the patient or after the lamina plate is positioned in the patient and before or after inserting bone screws or other fixation elements to attach the plate to a vertebra. By installing the bone screws before attaching the one or more receiver heads, the surgeon can be provided with adequate clearance to insert the bone screws along the trajectories disclosed herein, which minimizes or eliminates the need for additional lateral exposure of the vertebra. Inserting the receiver heads after the lamina plate is positioned in the patient can also improve a surgeon's ability to navigate anatomical structures. The steps of inserting a lamina plate, securing a plate to a vertebra via fixation elements, and coupling one or more receiver heads to a plate can be repeated for multiple vertebrae, at any level of the spine. In some embodiments, pedicle screws or other fixation elements can be inserted into a vertebra and coupled to a receiver head without a lamina plate. With the receiver heads and plates so positioned, a stabilization element, e.g., a rod, can be inserted through the receiver heads. The receiver heads can be pivoted or otherwise angularly oriented as desired so that the stabilization element can be inserted therethrough. A locking element, e.g., a set screw or locking nut, can be inserted into each of the receiver heads to angularly lock each receiver head relative to the plate and/or to attach the stabilization element to the receiver heads. These steps can be repeated for a second stabilization element, such as when bilateral stabilization is desired. After the desired stabilization is achieved, the incision can be closed.

Figure 15A:
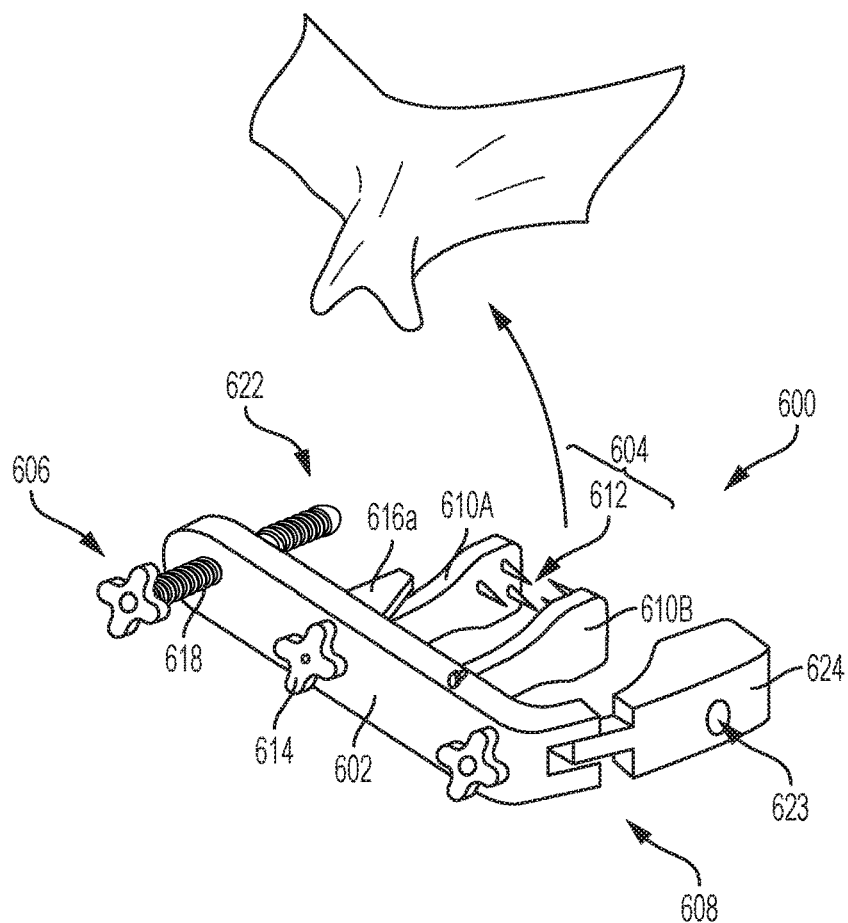
FIG. 15A is a perspective view of a guide instrument that can be used prior to performing a laminectomy to determine a trajectory for fixation elements.
Figure 15B:
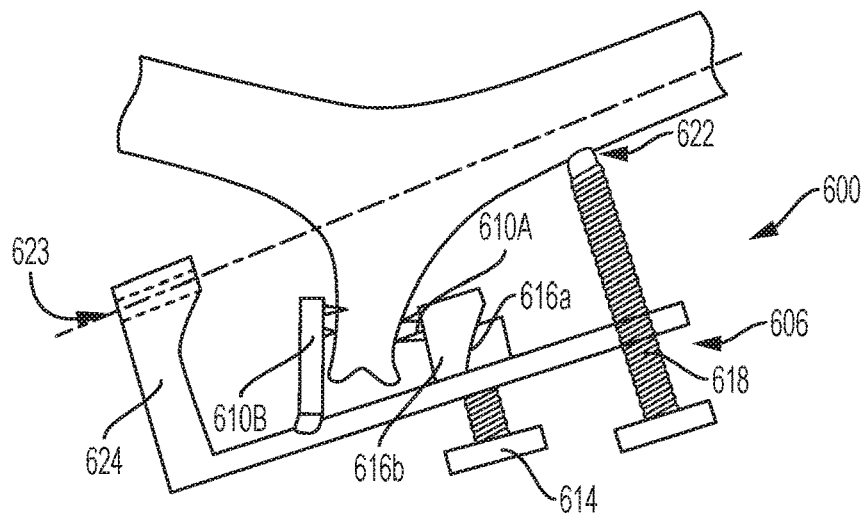
FIG. 15B is a superior view of the guide instrument of FIG. 15A coupled to a spinous process of a vertebra.
Figure 15C:
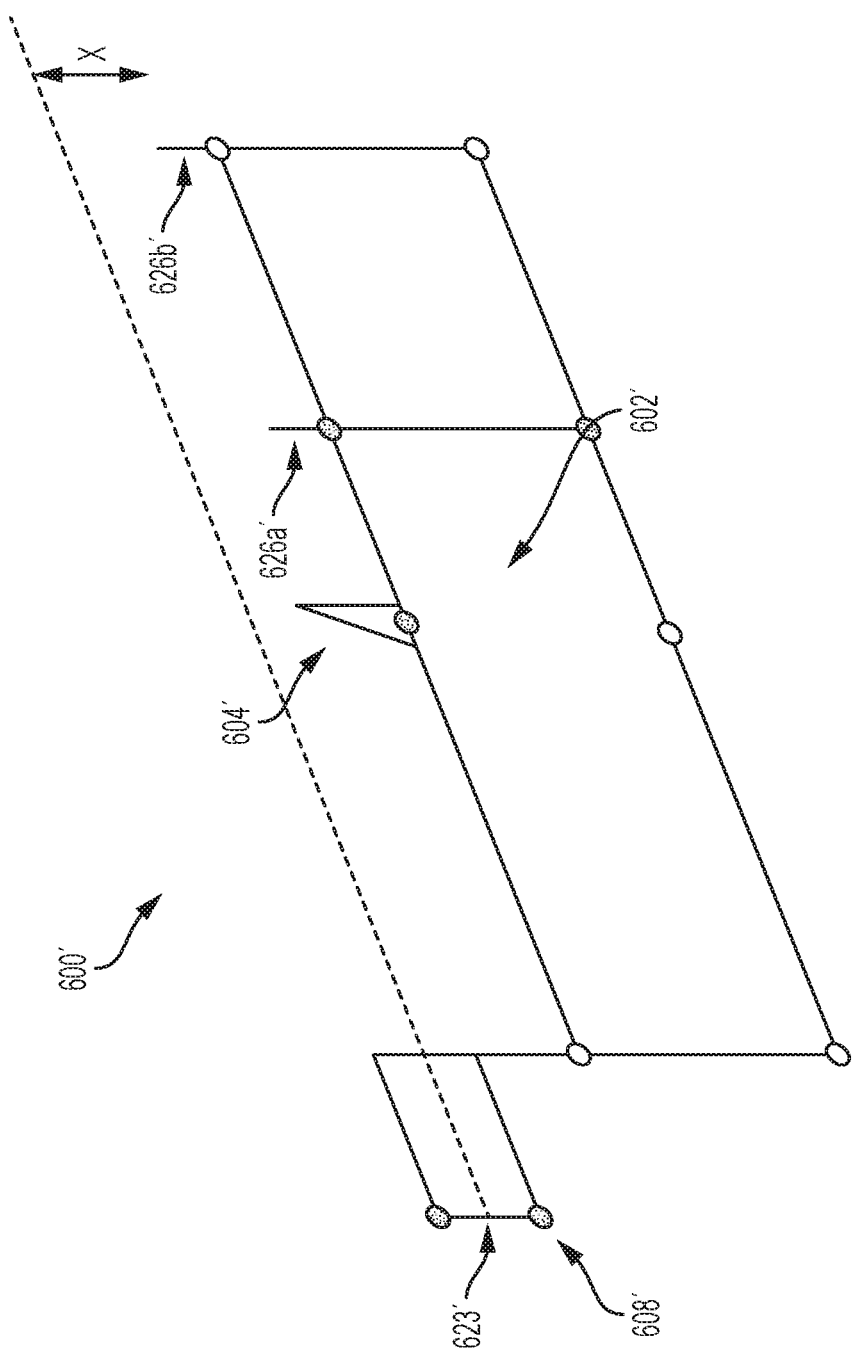
FIG. 15C is a schematic diagram of a guide instrument.

FIGS. 15A-15C illustrate a guide instrument 600 that can allow fixation elements (not shown) to be inserted into a vertebra before the spinous process and the laminae are removed. This can advantageously minimize the usage of pointed and sharp instruments when the spinal cord is exposed after laminectomy. As shown, the guide instrument 600 can include a horizontal body 602 that includes a clamping member 604, an adjustable stop 606, and a guide sleeve 608. The guide instrument 600 can couple to a vertebra in various ways, such as via a fixation pin or screw inserted into a posterior most end of the spinous process or via the illustrated clamping member 604 which engages first and second lateral sides of the spinous process. For example, FIG. 15A shows a guide instrument 600 having the clamping member 604 disposed at a central portion of the instrument 600 that fixedly couples to the spinous process.

The clamping member 604 can have various configurations, but in the illustrated embodiment includes first and second arms 610a, 610b that can lock onto opposite sides of the spinous process. The arms 610a, 610b can have various surface features 612 to increase a locking strength between the instrument 600 and the spinous process, such as spurs, needles, etc. The clamping member 604 can be selectively locked onto the spinous process by rotating a knob 614 to advance a threaded shaft and cause a first cam block 616a to slide with respect to a second cam block 616b to decrease a horizontal distance between the arms 610a, 610b, as shown in FIG. 15B.

A first lateral end of the instrument 600 can include an adjustable stop 618 such as a threaded member 620 that can be advanced or retracted as desired so that a distal end 622 of the stop 618 contacts a lamina. This can ensure that the horizontal member 602 of the instrument 600 is parallel to the lamina, as shown in FIG. 15B. Alternatively, the adjustable stop could be used to accommodate other trajectories that are parallel to the horizontal member 602. The instrument 600 can have a guide sleeve 608 disposed on a second lateral end of the instrument 600 that includes a guide arm 624. As shown, the guide sleeve 608 has an opening 623 formed in the arm 624 that defines a trajectory parallel to the horizontal member 602. The instrument 600 can thus establish a trajectory into the lamina which can be used for drilling, tapping, and/or screw insertion.

As will be appreciated, the instrument 600 can vary in any number of ways. For example, FIG. 15C schematically illustrates a guide instrument 600' having a horizontal member 602', a guide sleeve 608', and a fixation pin 604' rather than a clamping member. This guide instrument 600' also has first and second lamina docking points 626a', 626b' that can couple to a lamina (not shown). Regardless of a position of the instrument 600' relative to a vertebra, there is a fixed depth x between the guide sleeve 608' and the docking points 626a', 626b'.

FIGS. 16A-16E illustrate an exemplary embodiment of a "screw first" method. As in the methods described above, the method can include forming one or more incisions in a patient's body and retracting muscle and tissue to access a target vertebra, e.g., a cervical vertebra, and the degree of exposure of the vertebra can be less than in traditional procedures where a fixation element is inserted directly into a lateral mass, rather than through a lamina. This can reduce trauma to the patient and facilitate healing because larger incisions and greater dissection in a lateral direction tends to increase a patient's blood loss. In this embodiment, fixation elements 200A, 200B can be inserted into a vertebra prior to performing the laminectomy and also prior to installing the lamina plate on the vertebra. As will be appreciated, this can decrease a risk to the spinal cord because the spinal cord will remain protected by both the laminae and the spinous process during drilling and insertion of the fixation elements.

Figure 16A:
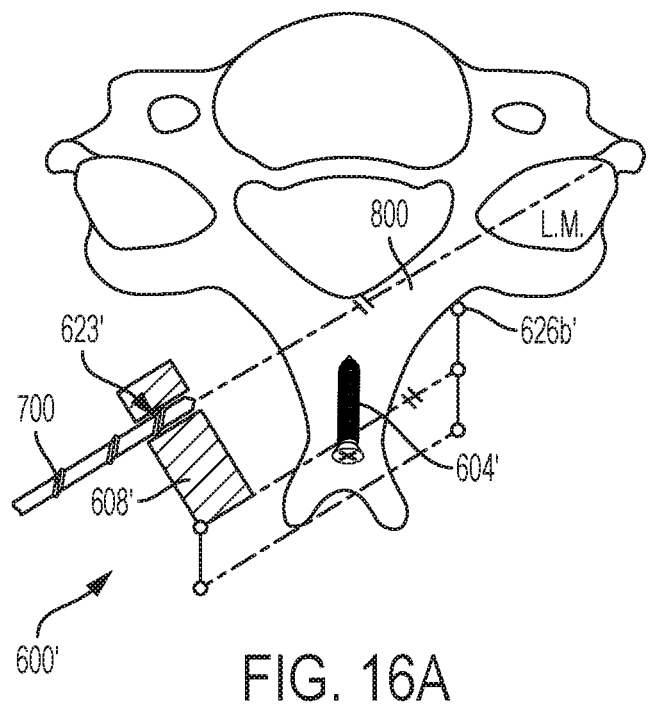
FIG. 16A is a superior view of the guide instrument of FIG. 15C coupled to a vertebra and having a drill extending through the instrument.
Figure 16B:
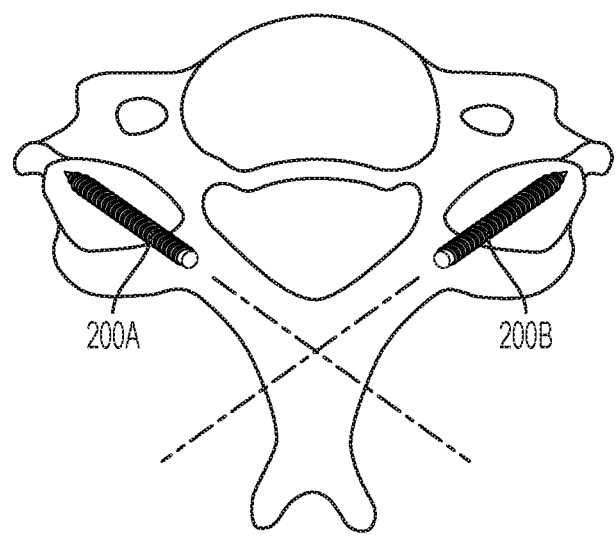
FIG. 16B is a superior view of the vertebra having fixation elements extending into the lateral mass.

FIG. 16A illustrates the guide instrument 600' coupled to a vertebra and more specifically, a spinous process. As shown, a drill 700 can be inserted through a guide sleeve 608 and can be angled so that it follows a trajectory through a lamina 800 and into a first lateral mass L.M. of the vertebra. As will be appreciated, an angle of the drill (not shown) relative to a midline of the vertebra can be in the range of ° MIN to θMAX as in FIGS. 11A and 11B. Once the desired angle is set using the instrument 600', the instrument 600' can be locked at this angle and the drill 700 can be advanced distally along the trajectory following the anatomy of the vertebra. A distal tip of the drill 700 can be advanced until it reaches a desired end point, such as in the lamina or the lateral mass, to form a pathway into the bone. A fixation element 200A, e.g., a bone screw, can be inserted into the vertebra through the pathway, such as via the guide sleeve 608' of the instrument 600'. These steps can be repeated for a second fixation element 200B, e.g. bone screw. In a cervical vertebra, a distal end of each of the fixation elements 200A, 200B can be positioned at a distal most position in the lateral mass L.M., as shown in FIG. 16B. As also shown in FIG. 16B, the fixation elements 200A, 200B can be advanced into the vertebra such that the proximal ends of the fixation elements are recessed below a plane at which the lamina is to be cut in a subsequent step. To facilitate such placement, the fixation elements 200A, 200B can be screws having a low profile head with a maximum outer diameter that is less than or equal to a maximum outer diameter of the threaded shank of the screw.

Figure 16C:
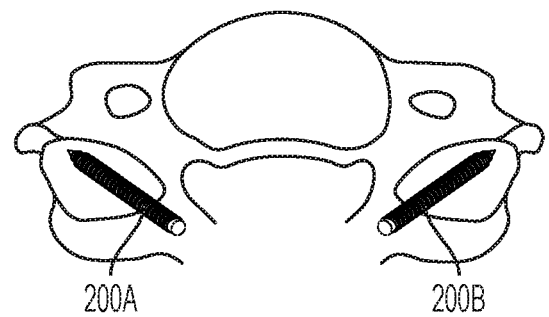
FIG. 16C is a superior view of the vertebra after the spinous process and the laminae have been removed.
Figure 16D:
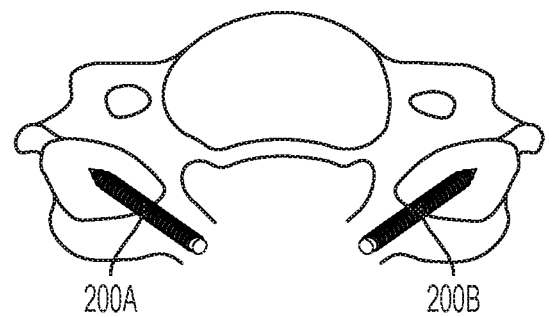
FIG. 16D is a superior view of the vertebra having fixation elements that are retracted proximally to prepare for mating with a lamina plate.
Figure 16E:
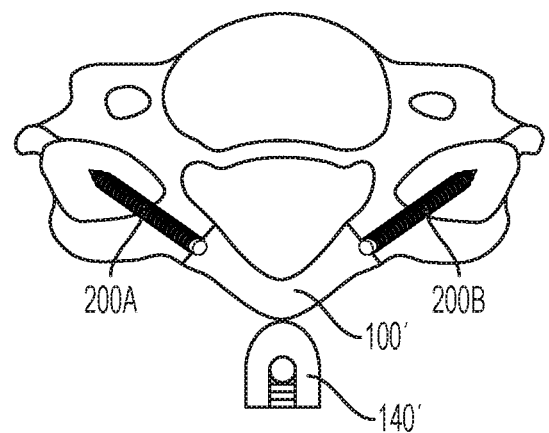
FIG. 16E is a superior view of the vertebra having a lamina plate coupled to the fixation elements.

After the first and second fixation elements 200A, 200B are inserted into the vertebra, a full laminectomy can be performed as shown in FIG. 16C. As in the embodiments above, a full laminectomy can be performed on the target vertebra and the cuts formed thereon can be shaved, contoured, or otherwise modified to prepare the cut surface for coupling to a lateral end of a lamina plate. Relative distances between the cut surfaces can be the same as discussed above. The first and second fixation elements 200A, 200B can then be moved proximally (e.g., by reverse rotating in the case of screws) as shown in FIG. 16D such that they protrude from the cut lamina ends and are ready to receive a lamina plate. As shown in FIG. 16E, a lamina plate 100' can then be installed onto the protruding fixation elements 200A, 200B.

In particular, a lamina plate can be inserted in the patient and positioned in an installed position, e.g., a position in which a first lateral end of the plate contacts and/or receives the first cut portion of the vertebra and a second lateral end of the plate contacts and/or receives the second cut portion of the vertebra such that the plate spans across the first and second cut lamina ends of the vertebra. The lamina plate 100' can have any of the features described herein, such as the features that allow it to move between compressed and expanded positions to better accommodate the surgical site as shown in FIGS. 2C and 2D. After the lamina plate 100' is installed, one or more receiver heads 140' can be coupled to the plate or to the fixation elements 200A, 200B, or instead the plate 100' can be used alone as a prosthesis that does not require a receiver head and stabilization elements.

Figure 17A:
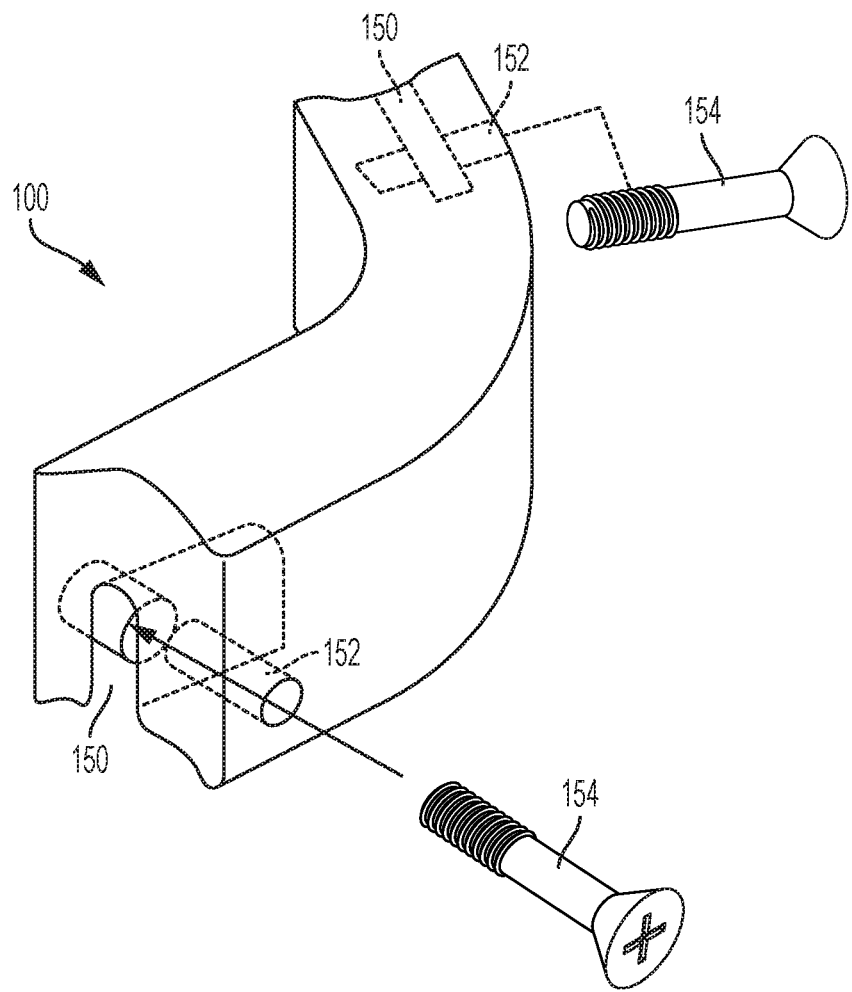
FIG. 17A is a perspective view of a lamina plate with slots for receiving fixation elements.
Figure 17B:
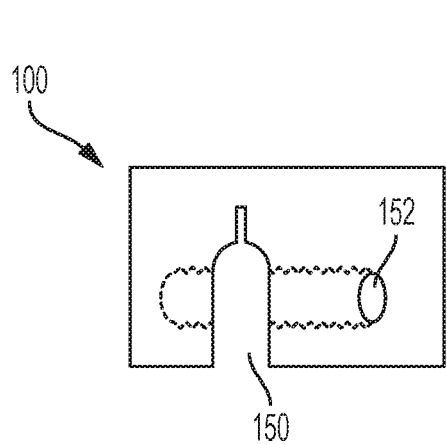
FIG. 17B is an end view of the lamina plate of FIG. 17A.
Figure 17C:
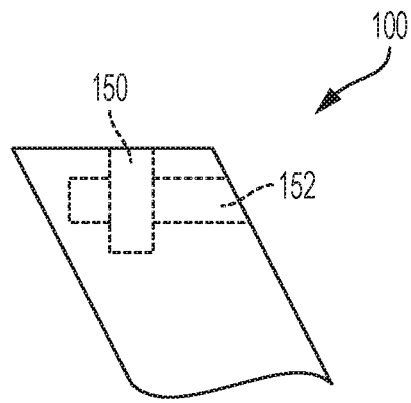
FIG. 17C is a partial superior view of the lamina plate of FIG. 17A.

The lamina plate can have any of a variety of features to facilitate use in a screw-first technique of the type describe above. For example, in the embodiment shown in FIGS. 2C-2D, the lamina plate can be transitioned to the expanded configuration such that it expands into engagement with the fixation elements 200A, 200B and securely attaches thereto. By way of further example, the lamina plate can include one or more hooks or slots in which the fixation elements 200A, 200B can be received. FIGS. 17A-17C illustrate an exemplary embodiment of a lamina plate 100 that includes slots 150 for receiving the portions of the fixation elements 200A, 200B that protrude from the cut laminae. Each slot 150 can extend inward from a lateral end of the plate 100 along an axis that is substantially collinear with the central longitudinal axis of the fixation element 200 that is to be received within the slot. The plate 100 can also include one or more openings 152 corresponding to respective ones of the one or more slots 150 through which a locking mechanism 154 can be received to lock a fixation element within the slot. For example, as shown, each of the slots 150 includes an opening 152 that extends perpendicular thereto in which a locking screw 154 can be received. Once the fixation element 200 is positioned within the slot 150, the locking screw 154 can be advanced within the opening 152 to engage the fixation element and secure it within the slot. In some embodiments, the locking screws 154 can include receiver heads formed at a proximal end thereof in which a spinal stabilization element can be received.

Figure 18:
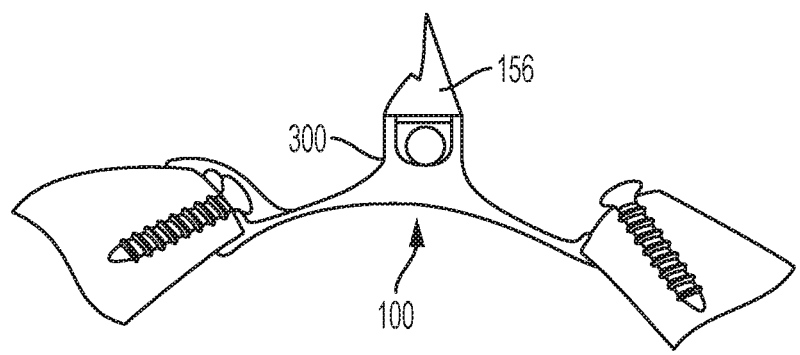
FIG. 18 is a superior view of a lamina plate having a spinal stabilization element disposed in the receiver head and tissue-growth promoting material coupled thereto.

Any of the systems and devices herein can be used with biological material that promotes soft tissue healing, such as small intestine submucosa (SIS), dermis, and pericardium materials. Such materials can provide an enhanced bonding surface that causes tissue to heal around it and can integrate onto a surface of metal, plastic, etc. The biomaterials, for example, can be extracted from a variety of sources, such as porcine, bovine, equine, and human. The material can be attached to the devices herein at various locations, such as along one or more receiver heads, along a posterior surface of a lamina plate, and/or along a stabilization element extending through a plurality of receiver heads. For example, FIG. 18 illustrates a receiver head 300 of a lamina plate 100 having a biological material 156 coupled thereto and extending in a posterior direction from the receiver head 300. As will be appreciated, attachment between the biological material and the devices can be achieved in various ways. For example, a surgeon can manually position the material onto devices such as the lamina plate after the devices are implanted in a patient and can optionally suture this material to the patient's tissue. In another embodiment, the lamina implant, receiver head, and/or stabilization element can be modified during a manufacturing process to include a biological surface finish that promotes adhesion of tissue.

The devices herein can be formed from a variety of biocompatible materials that can be inserted in a patient's body. Exemplary material for forming the plates, screws, receiver heads, etc. include, by way of non-limiting example, stainless steel, titanium, polymers, ceramics, allograft, and/or combinations thereof. As previously described, the spinal stabilization elements can have a variety of properties, and, by way of non-limiting example, can be rigid, semi-rigid, bendable, flexible, etc. Exemplary material for forming the stabilization elements include, by way of non-limiting example, stainless steel, titanium, polymers, ceramics, and/or combinations thereof.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A spinal implant, comprising:
 a body having an anterior surface, a posterior surface, a superior surface, and an inferior surface, the body being positionable with respect to a vertebra on which a laminectomy has been performed in an installed position in which a first terminal end surface of the body receives at least a portion of a first cut lamina end of the vertebra and a second, opposite terminal end surface of the body receives at least a portion of a second, opposite cut lamina end of the vertebra such that the body spans across the first and second cut lamina ends of the vertebra;
 a first bone anchor receiving hole formed through the posterior surface of the body and exiting though the first terminal end surface of the body and angled such that a bone screw inserted therethrough extends into a first lateral mass of a vertebra when the body is disposed in the installed position with respect to the vertebra;
 a second bone anchor receiving hole formed through the posterior surface of the body and exiting though the second terminal end surface of the body and angled such that a bone screw inserted therethrough extends into a second, opposite lateral mass of a vertebra when the body is disposed in the installed position with respect to the vertebra;
 at least one mating feature formed in the body to which a receiver head can be selectively coupled;
 a receiver head having a mating feature configured to selectively couple the receiver head to the at least one mating feature formed in the body; and
 an adjustment mechanism configured to adjust a degree of curvature of the body.

2. The implant of claim 1, wherein the at least one mating feature comprises a central mating feature disposed along a central superior-inferior axis of the body such that when the body is disposed in the installed position with respect to a vertebra, the central mating feature is positioned above a midline of the vertebra.

3. The implant of claim 1, wherein the at least one mating feature comprises first and second lateral mating features positioned laterally offset from a central superior-inferior axis of the body.

4. The implant of claim 1, wherein the at least one mating feature comprises threaded holes formed in the body.

5. The implant of claim 1, wherein the superior surface of the body defines a curved relief configured to receive a spinous process of a superior vertebra when the body is disposed in the installed position with respect to an adjacent inferior vertebra.

6. The implant of claim 1, wherein the body is curved about a central superior-inferior axis of the body such that the anterior surface of the body defines a curved relief for protecting a spinal cord when the body is disposed in the installed position with respect to a vertebra.

7. The implant of claim 1, wherein the receiver head is configured to be coupled to the body via at least one of a polyaxial coupling, a uniplanar coupling, and a monoaxial coupling.

8. The implant of claim 1, wherein the first bone anchor receiving hole extends at an angle in the range of about 120 degrees to about 140 degrees with respect to a plane in which a posterior-most extent of the body lies.

9. The implant of claim 1, wherein the adjustment mechanism is configured to move the body between a compressed position and an expanded position, the compressed position defining a higher degree of curvature than the expanded position.

10. The implant of claim 1, wherein the adjustment mechanism includes a threaded rod that extends through the body in an anterior-posterior direction.

11. The implant of claim 10, wherein the threaded rod is configured to couple to a receiver member.

12. The implant of claim 10, wherein the adjustment mechanism further comprises a nut threaded onto the threaded rod adjacent the posterior surface of the body and an expansion member coupled to the threaded rod adjacent the anterior surface of the body.

13. The implant of claim 12, wherein the anterior surface of the body comprise a recess configured to receive at least a portion of the expansion member therein.

14. The implant of claim 13, wherein the adjustment mechanism is configured to move the body between an expanded position and a compressed position by a user tightening or loosening the nut.

15. The implant of claim 14, wherein tightening the nut wedges the expansion member into the recess and moves the body towards the expanded position.

16. The implant of claim 1, wherein the body is formed from a resilient material.

17. The implant of claim 16, wherein the body is biased towards a compressed position.

18. A spinal implant, comprising:
a body having an anterior surface, a posterior surface, a superior surface, and an inferior surface, the body being positionable with respect to a vertebra on which a laminectomy has been performed in an installed position in which a first terminal end surface of the body receives at least a portion of a first cut lamina end of the vertebra and a second, opposite terminal end surface of the body receives at least a portion of a second, opposite cut lamina end of the vertebra such that the body spans across the first and second cut lamina ends of the vertebra;
a first bone anchor receiving hole formed through the posterior surface of the body and exiting though the first terminal end surface of the body and angled such that a bone screw inserted therethrough extends into a first lateral mass of a vertebra when the body is disposed in the installed position with respect to the vertebra;
a second bone anchor receiving hole formed through the posterior surface of the body and exiting though the second terminal end surface of the body and angled such that a bone screw inserted therethrough extends into a second, opposite lateral mass of a vertebra when the body is disposed in the installed position with respect to the vertebra;
at least one mating feature formed in the body to which a receiver head can be selectively coupled; and
an adjustment mechanism configured to adjust a degree of curvature of the body,
wherein the at least one mating feature comprises a central mating feature disposed along a central superior-inferior axis of the body such that when the body is disposed in the installed position with respect to a vertebra, the central mating feature is positioned above a midline of the vertebra.

19. The implant of claim 18, further comprising a receiver head having a mating feature configured to selectively couple the receiver head to the at least one mating feature formed in the body.

20. The implant of claim 18, wherein the adjustment mechanism includes a threaded rod that extends through the body in an anterior-posterior direction.

21. A spinal implant, comprising:
a body having an anterior surface, a posterior surface, a superior surface, and an inferior surface, the body being positionable with respect to a vertebra on which a laminectomy has been performed in an installed position in which a first terminal end surface of the body receives at least a portion of a first cut lamina end of the vertebra and a second, opposite terminal end surface of the body receives at least a portion of a second, opposite cut lamina end of the vertebra such that the body spans across the first and second cut lamina ends of the vertebra;
a first bone anchor receiving hole formed through the posterior surface of the body and exiting though the first terminal end surface of the body and angled such that a bone screw inserted therethrough extends into a first lateral mass of a vertebra when the body is disposed in the installed position with respect to the vertebra;
a second bone anchor receiving hole formed through the posterior surface of the body and exiting though the second terminal end surface of the body and angled such that a bone screw inserted therethrough extends into a second, opposite lateral mass of a vertebra when the body is disposed in the installed position with respect to the vertebra;
at least one mating feature formed in the body to which a receiver head can be selectively coupled; and
an adjustment mechanism configured to adjust a degree of curvature of the body,
wherein the adjustment mechanism includes a threaded rod that extends through the body in an anterior-posterior direction.

22. The implant of claim 21, wherein the threaded rod is configured to couple to a receiver member.

23. The implant of claim 21, wherein the adjustment mechanism further comprises a nut threaded onto the threaded rod adjacent the posterior surface of the body and an expansion member coupled to the threaded rod adjacent the anterior surface of the body.

\* \* \* \* \*